United States Patent [19]

Heimes

[11] Patent Number: 4,611,578
[45] Date of Patent: Sep. 16, 1986

[54] REDUNDANT PISTON PUMP FOR THE OPERATION OF SINGLE OR MULTIPLE CHAMBERED PNEUMATIC BLOOD PUMPS

[75] Inventor: Horst P. Heimes, Aachen, Fed. Rep. of Germany

[73] Assignee: Forschungsgesellschaft fur Biomedizinischs Technik E.V. Goethestrasse, Aachen, Fed. Rep. of Germany

[21] Appl. No.: 604,994

[22] Filed: Apr. 27, 1984

[30] Foreign Application Priority Data

May 3, 1983 [DE] Fed. Rep. of Germany ....... 3316101

[51] Int. Cl.$^4$ .......................... A61F 2/22; F04B 35/02; F04B 49/08
[52] U.S. Cl. .................... 128/1 D; 417/19; 417/383; 417/53
[58] Field of Search .............. 128/1 D; 3/1.7; 417/18, 417/19, 53, 45, 1, 3, 4, 5, 383, 389, 390, 374, 426, 429, 488, 339

[56] References Cited

U.S. PATENT DOCUMENTS

| 118,206 | 8/1871 | Crowell | 417/488 |
|---|---|---|---|
| 1,764,712 | 6/1930 | Brackett et al. | 417/439 |
| 1,832,257 | 11/1931 | Stephans | 417/339 |
| 3,428,042 | 2/1969 | Chestnut | 128/1 |
| 3,636,570 | 1/1972 | Nielson | 3/1.7 |
| 3,783,453 | 1/1974 | Bolie | 128/1 D |
| 3,874,002 | 4/1975 | Kurpanek | 3/1.7 |
| 3,911,897 | 10/1975 | Leachman | 128/1 D |
| 4,376,312 | 3/1983 | Robinson et al. | 417/395 |
| 4,397,049 | 8/1983 | Robinson et al. | 3/1.7 |
| 4,529,359 | 7/1985 | Sloan | 417/34 |

FOREIGN PATENT DOCUMENTS

| 2037851 | 2/1972 | Fed. Rep. of Germany . |
| 2454185 | 5/1976 | Fed. Rep. of Germany . |
| 3009012 | 12/1980 | Fed. Rep. of Germany ..... 128/1 D |
| 1064603 | 12/1953 | France . |
| 2476763 | 8/1981 | France . |
| 276870 | 8/1930 | Italy ................................... 417/389 |
| 79683 | 5/1983 | Japan ................................... 417/19 |

OTHER PUBLICATIONS

Biomedizinische Technik, vol. 24, No. 6, Jun. 1979, pp. 134-139, H. Thomas et al. "Ein Ausfallsicheres Antriebssystem fur Blutpumpen".

The International Journal of Artificial Organs, vol. 5, No. 3, 1982, pp. 157-159, H. P. Heimes et al. "Completely Integrated Wearable TAH-Drive Unit".

Primary Examiner—William L. Freeh
Attorney, Agent, or Firm—Spensley Horn Jubas & Lubitz

[57] ABSTRACT

A redundant, pneumatic driver for a blood pump in which a pair of pistons are contained in a common cylinder and their stroke rates and lengths are selectively controlled by a controller which non-invasively senses the circulatory system requirements of the patient in which the blood pump is implanted. The controller varies the stroke rates and lengths to meet such requirements and further is able to selectively switch driving functions from one piston to the other to provide a redundant driving capability.

10 Claims, 22 Drawing Figures

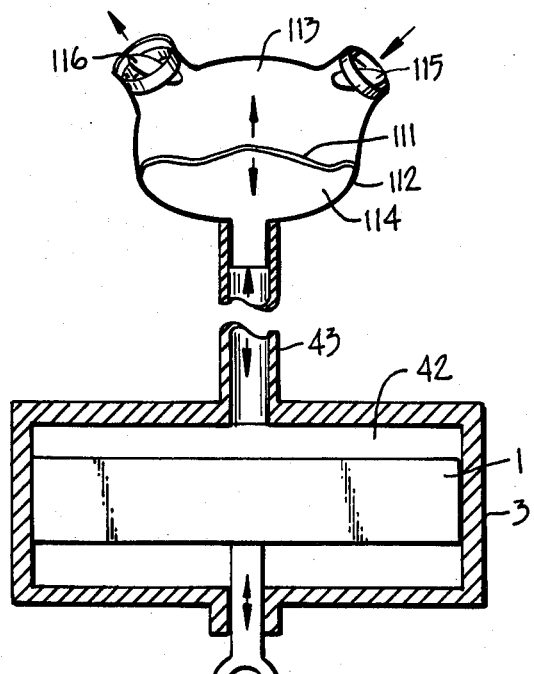
FIG._1. *PRIOR ART*
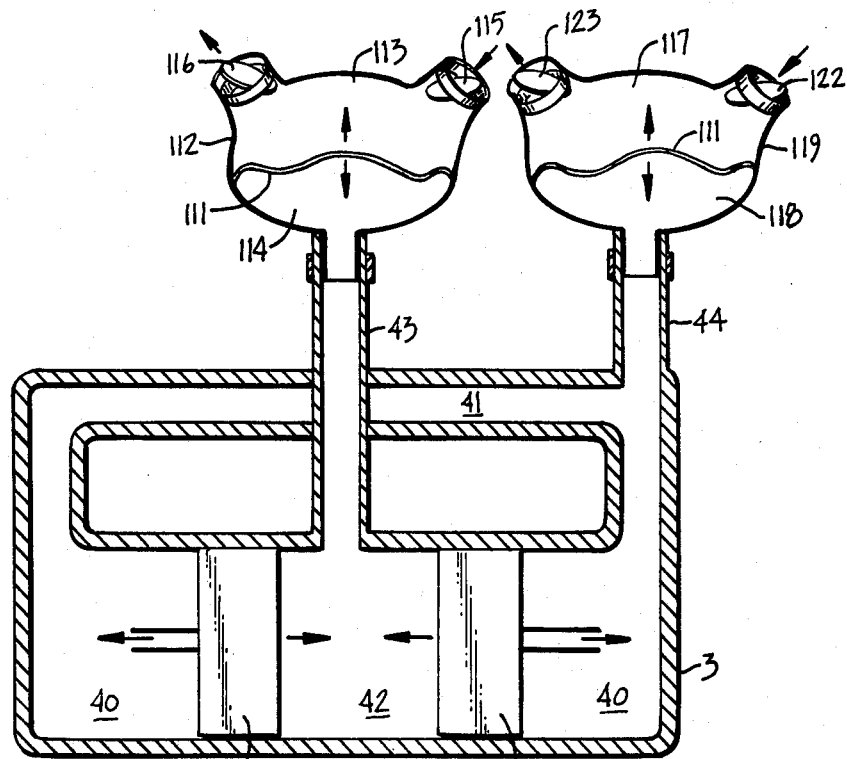
FIG._2.

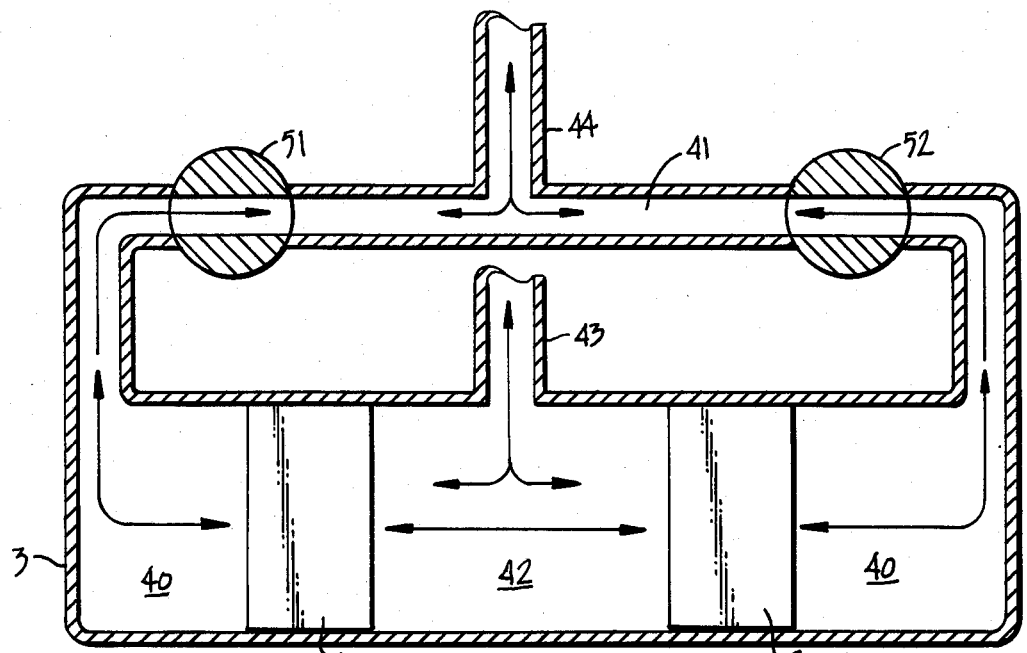
FIG._3.
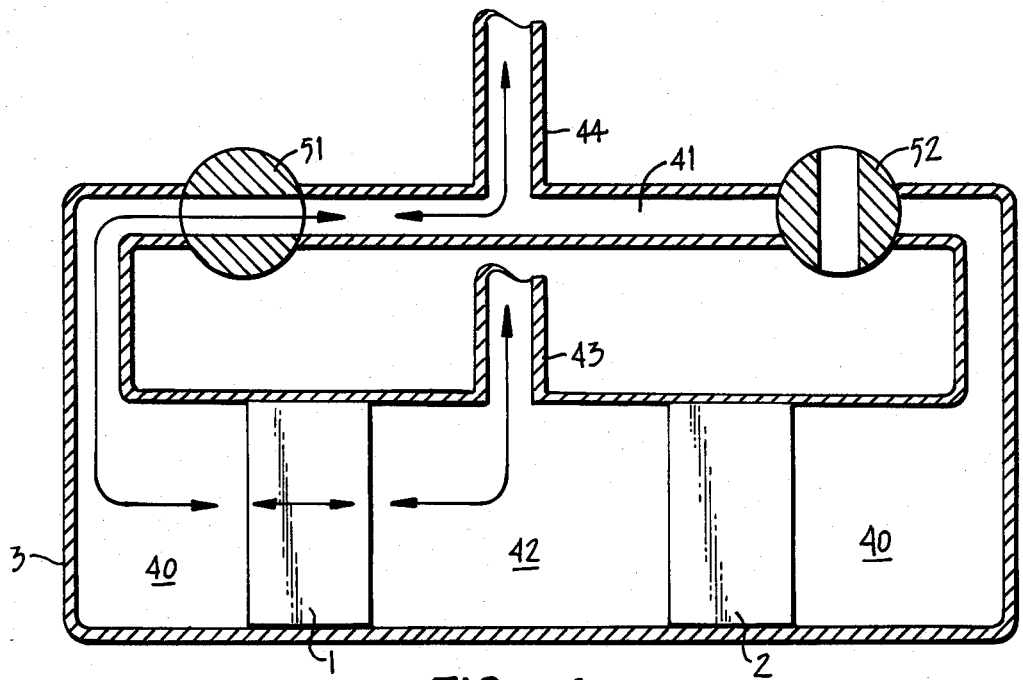
FIG._4.

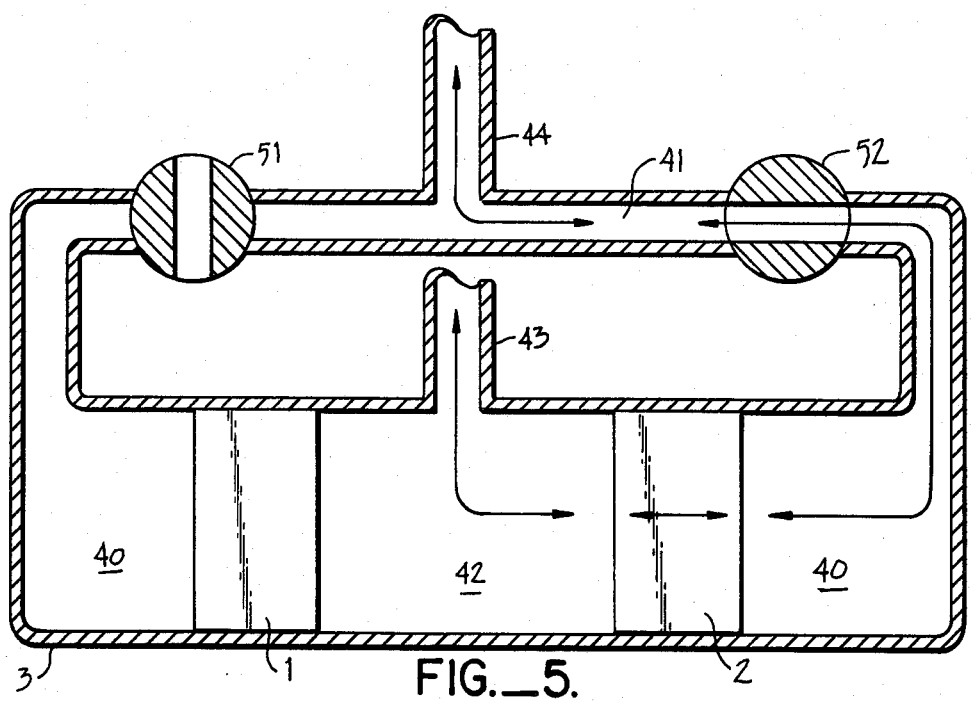
FIG._5.
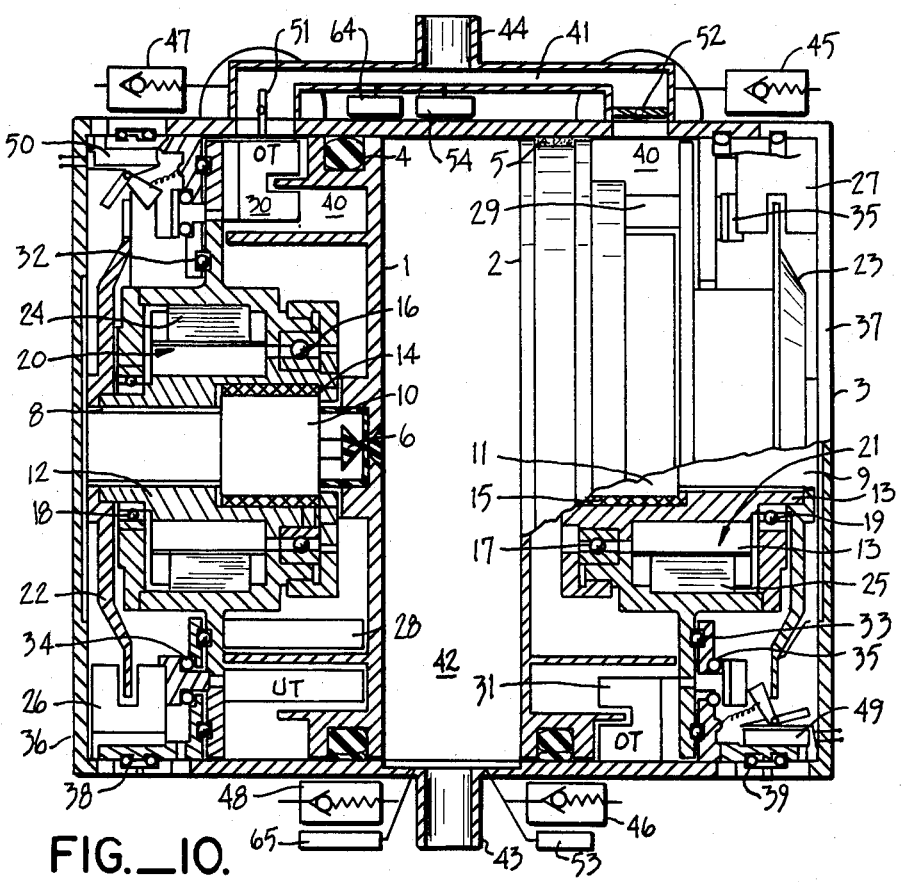
FIG._10.

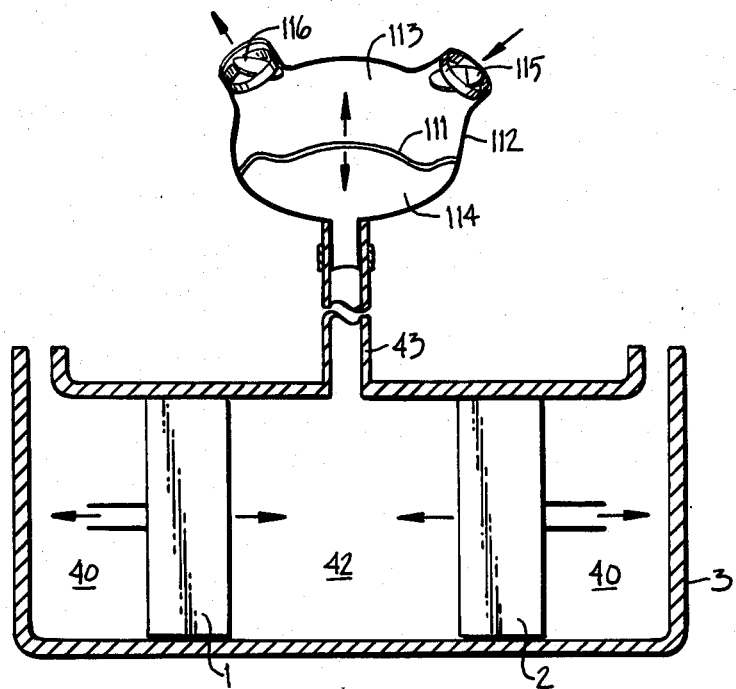
FIG._6.
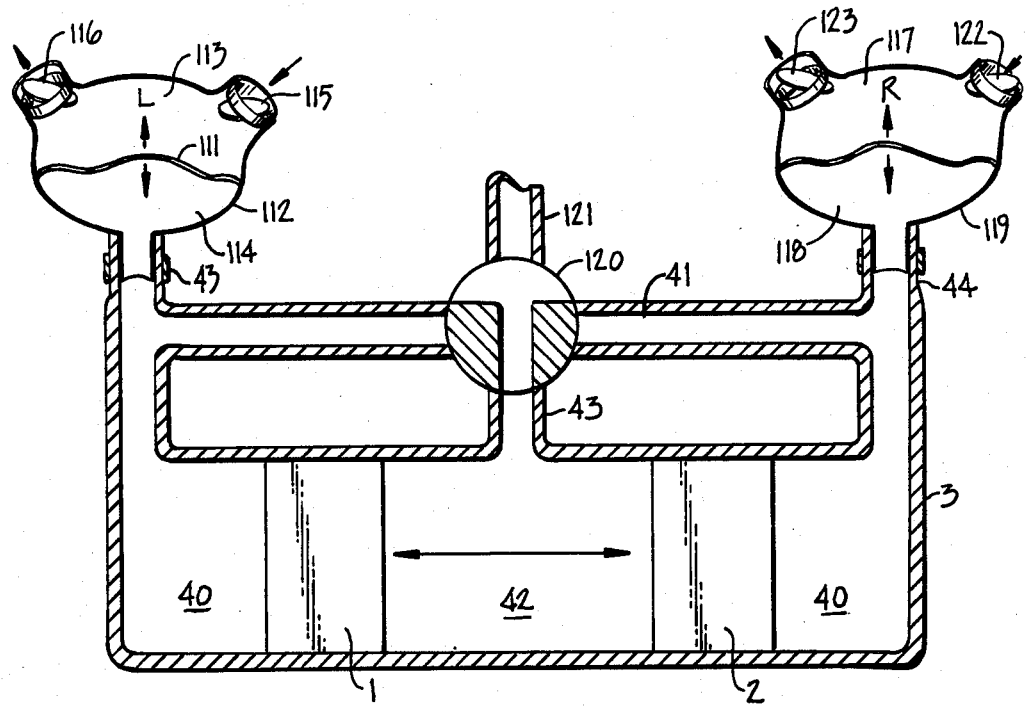
FIG._7.

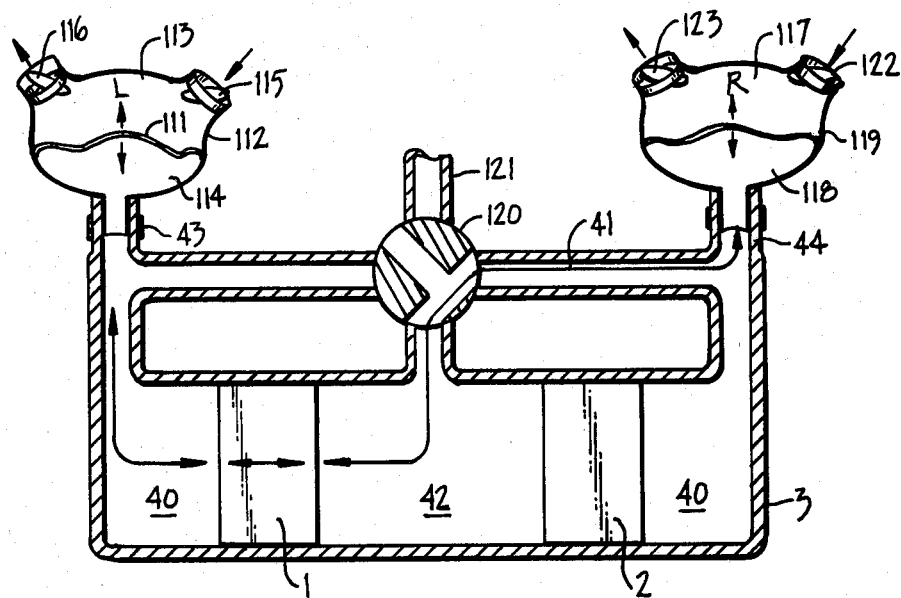
FIG._8.
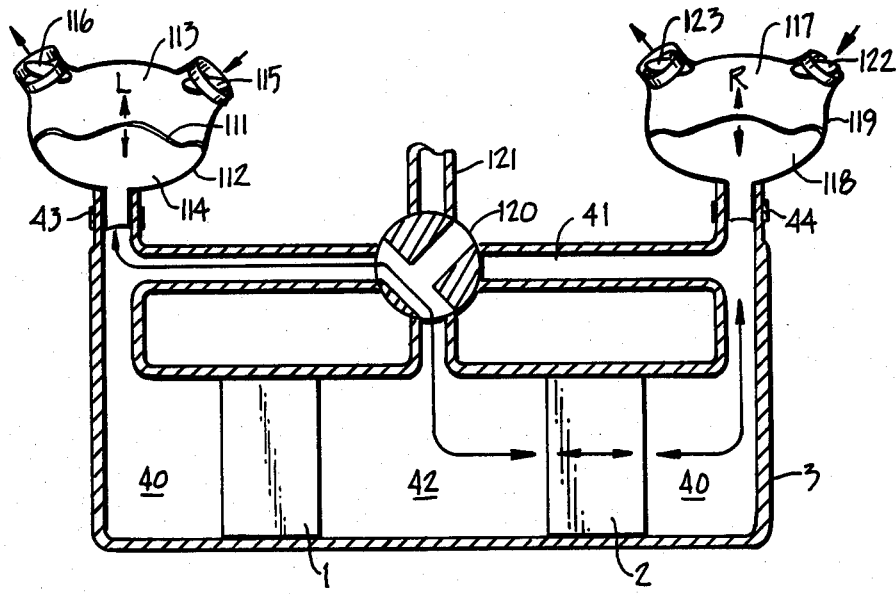
FIG._9.

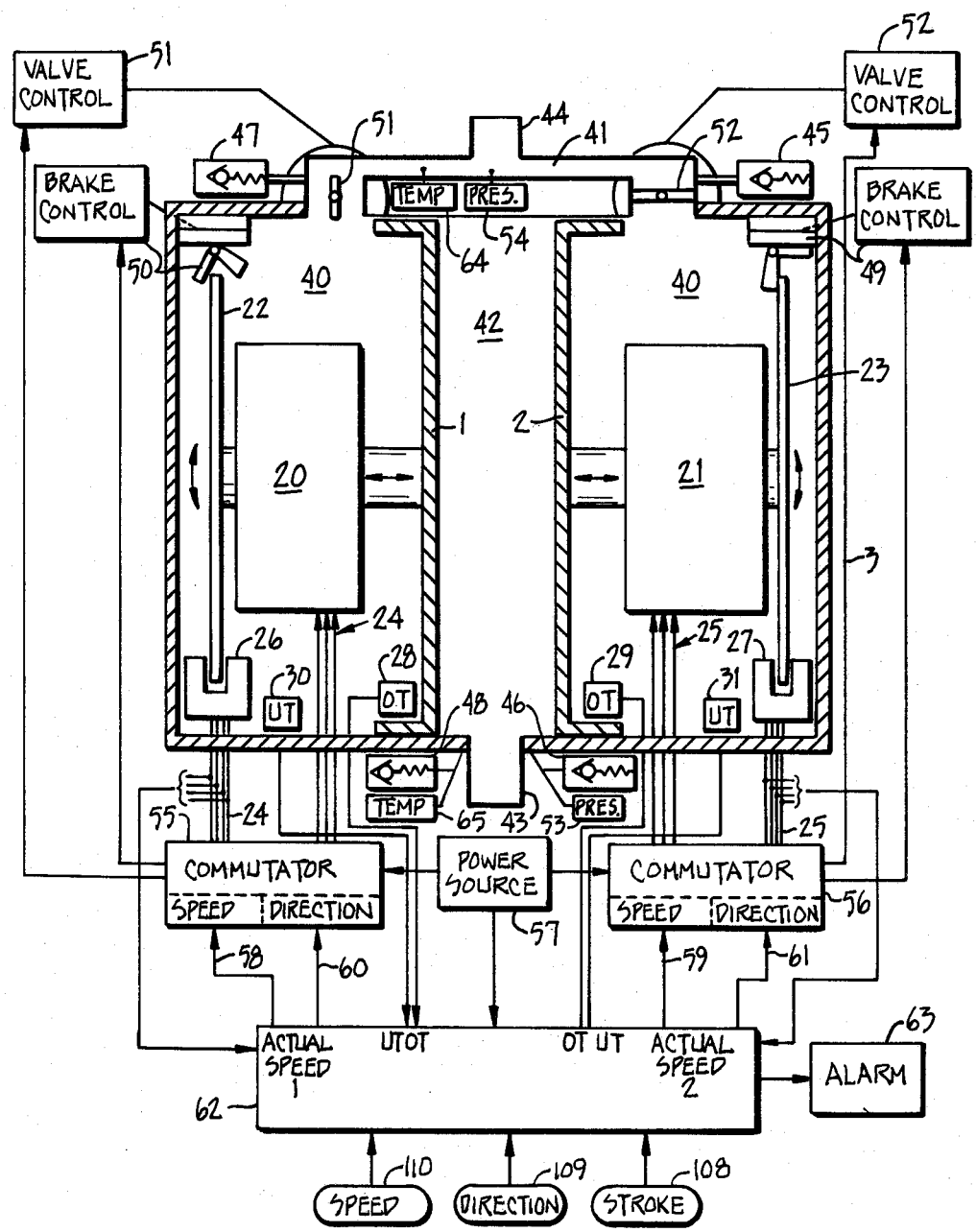
FIG._II.

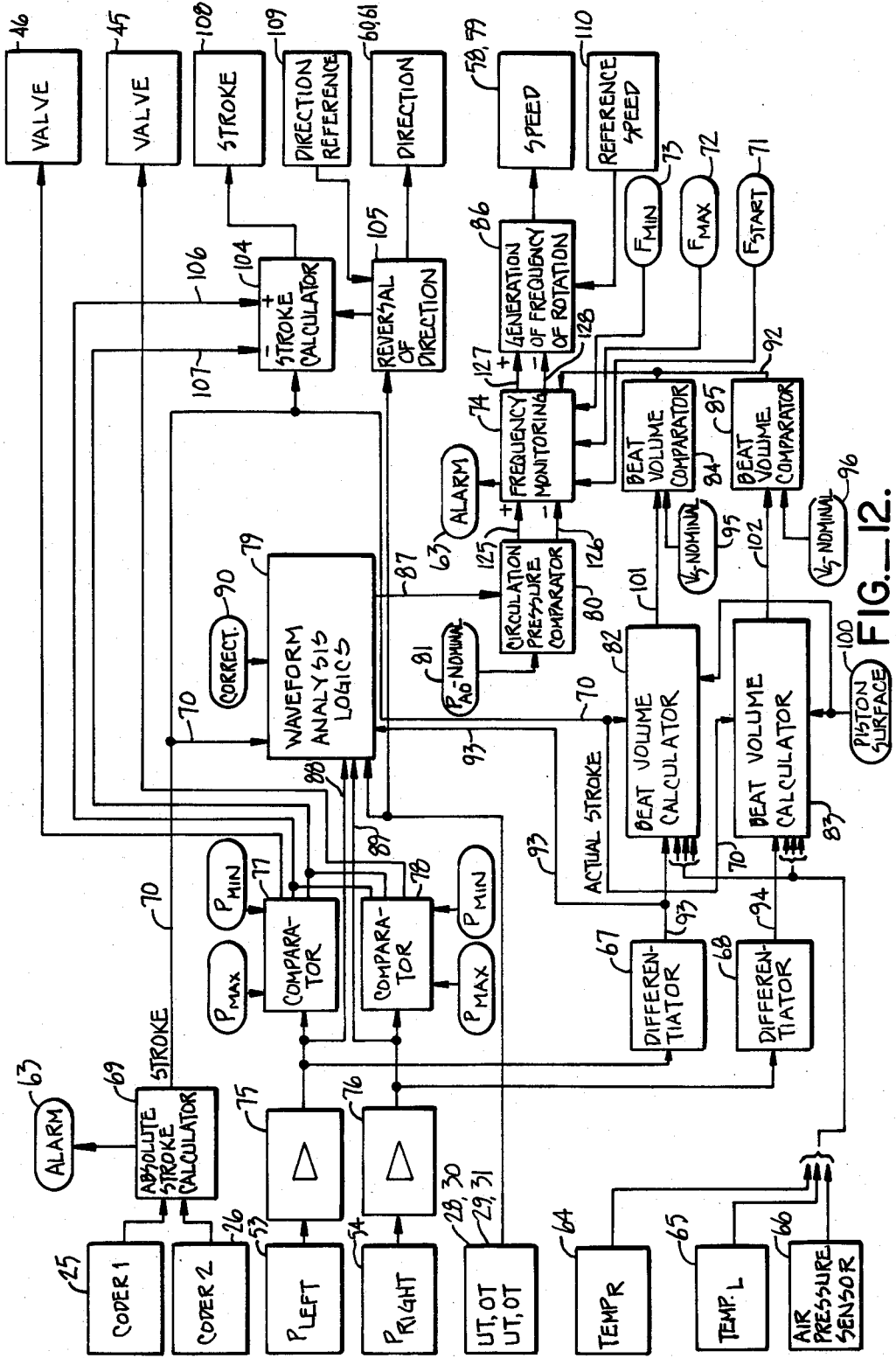

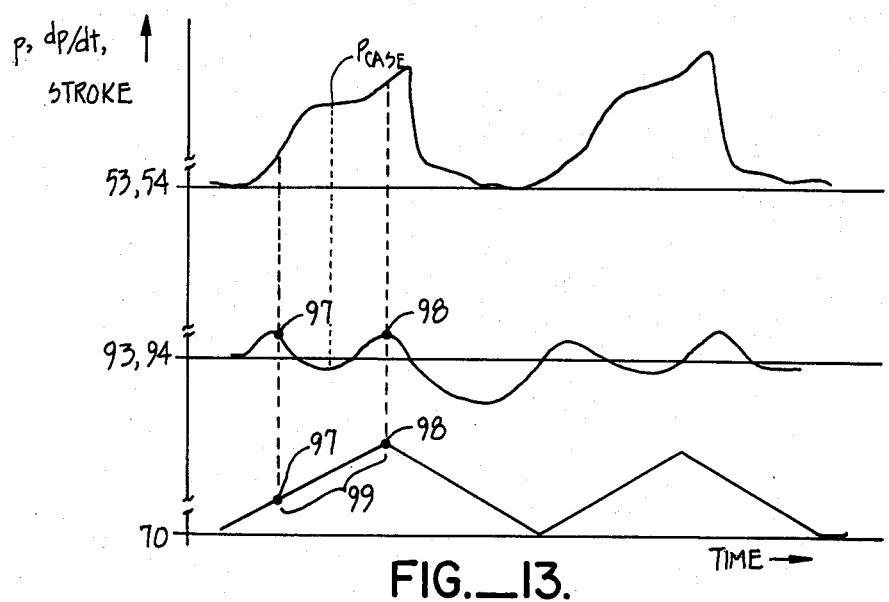
FIG._13.
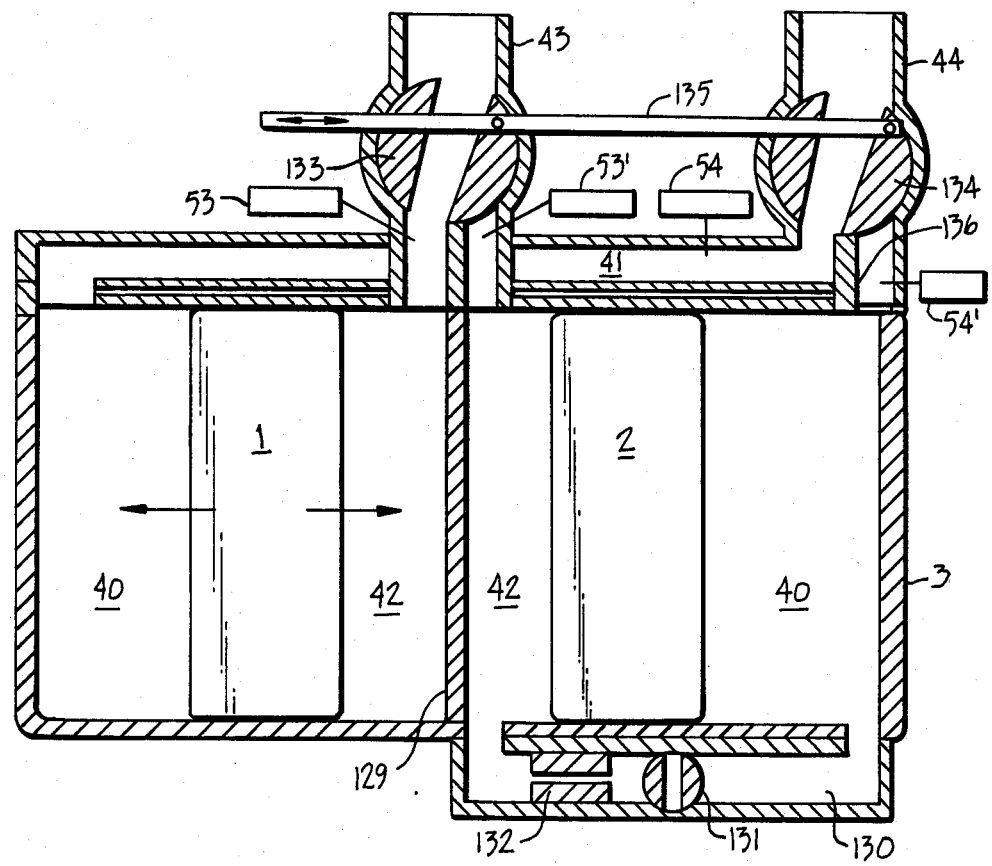
FIG._14.

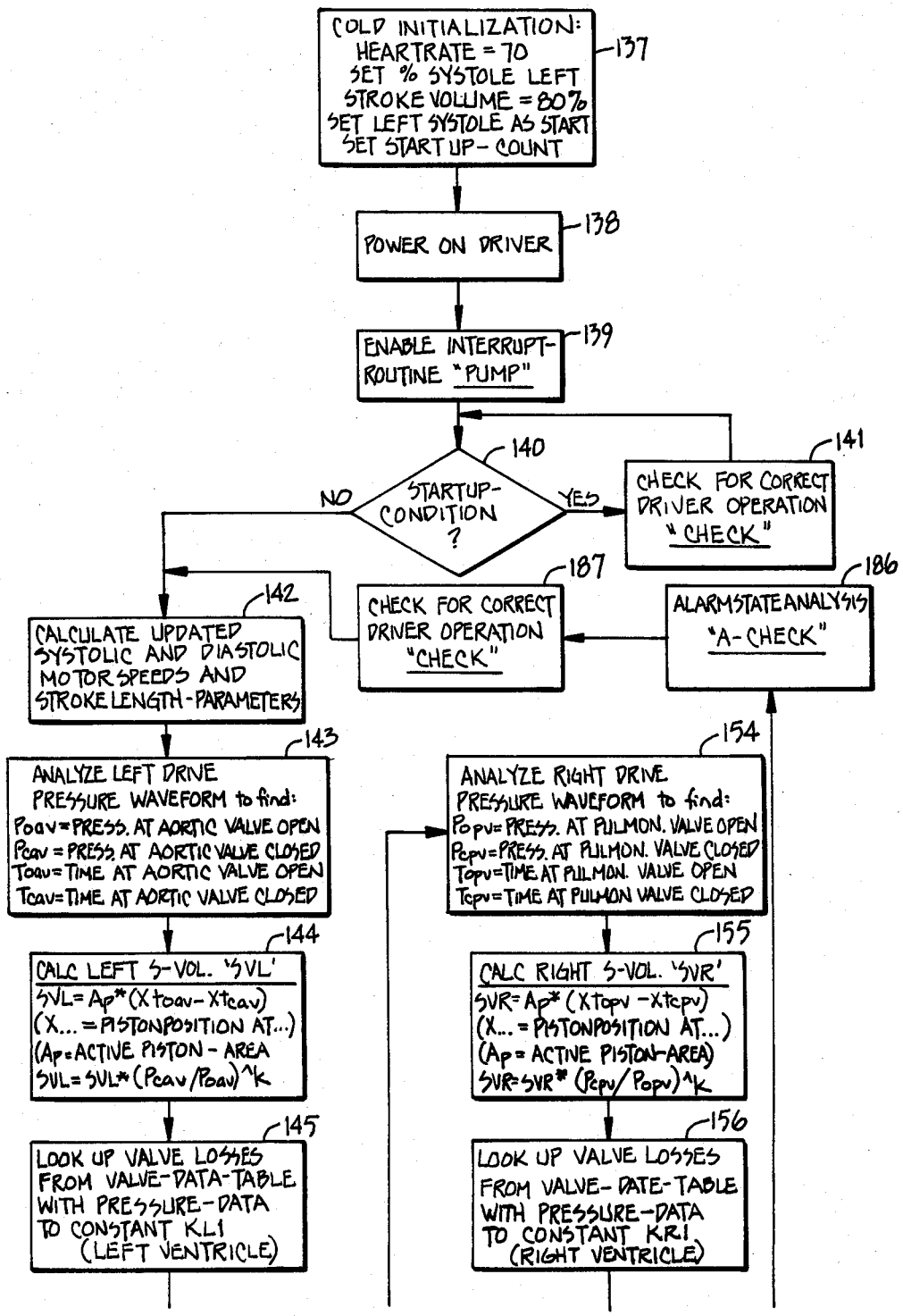
FIG._15A.

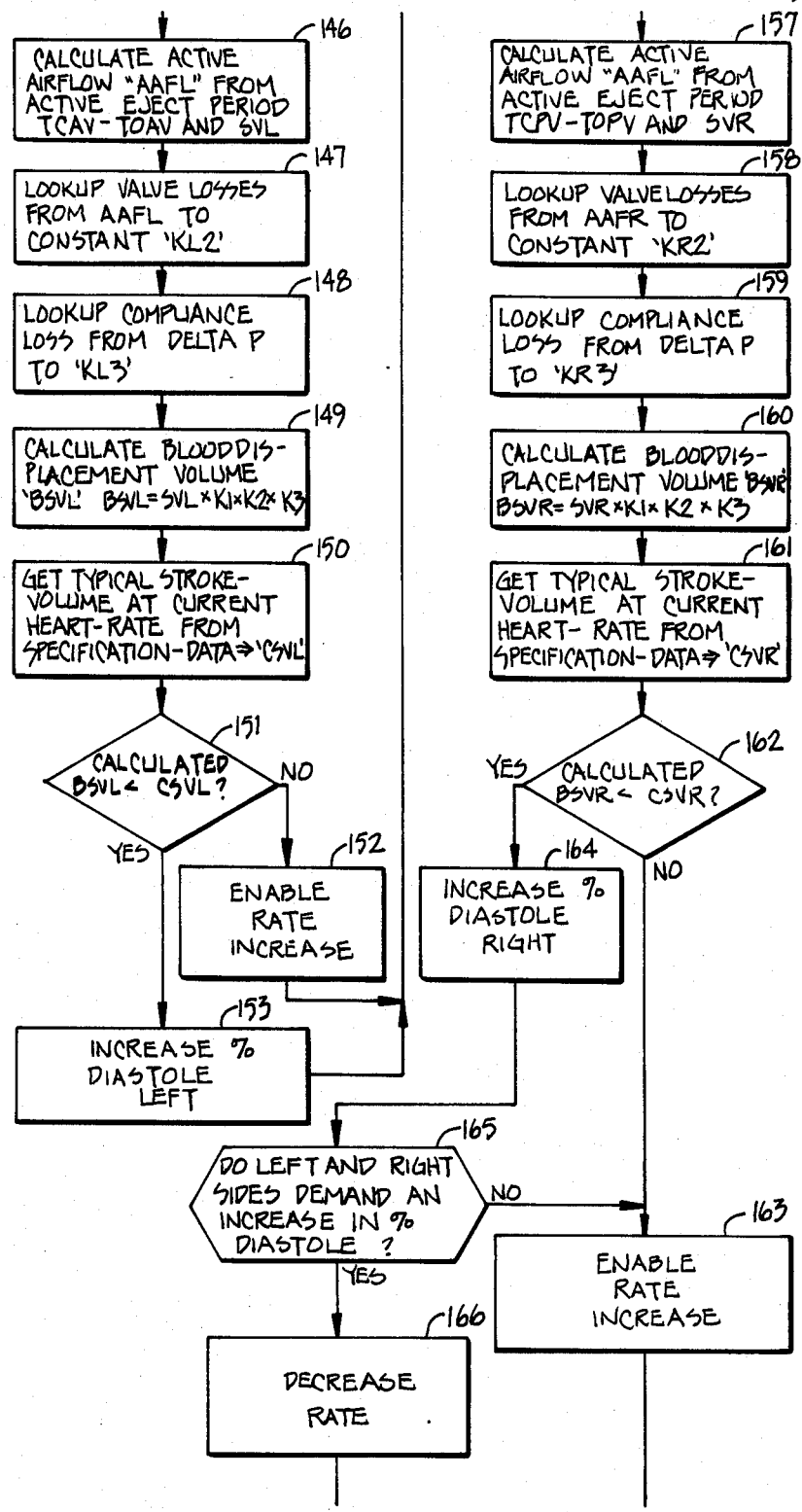
FIG._15B.

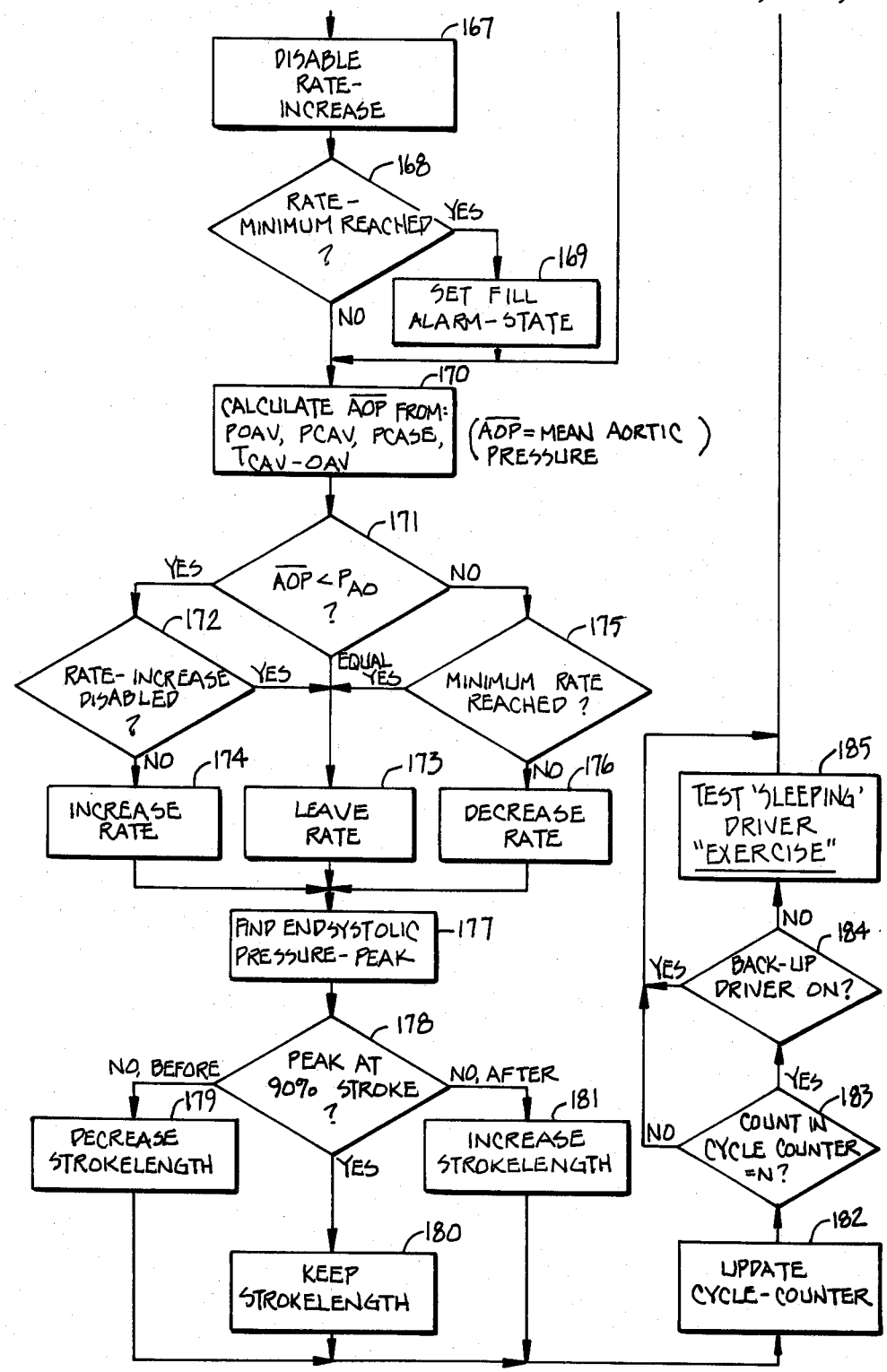
FIG._15C.

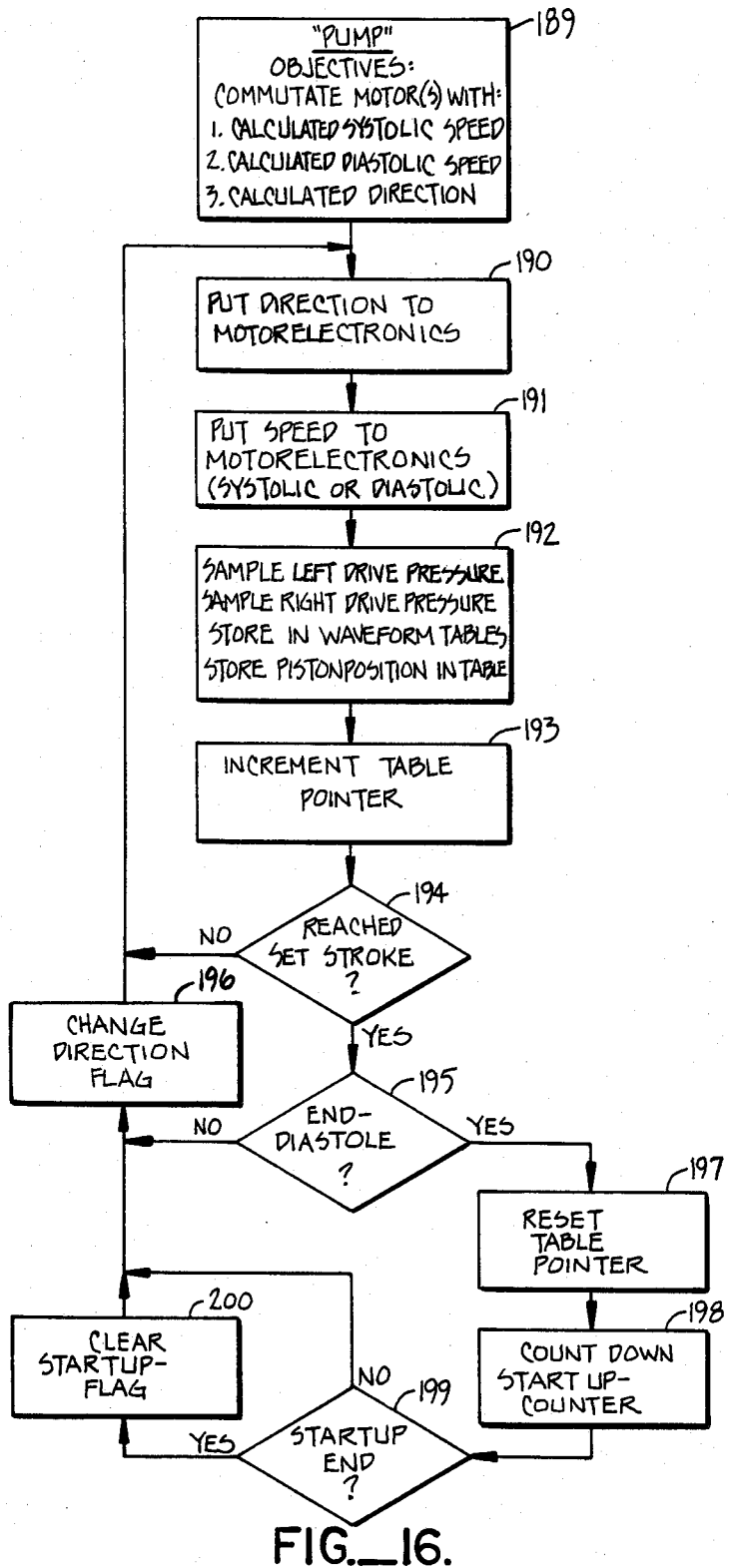
FIG._16.

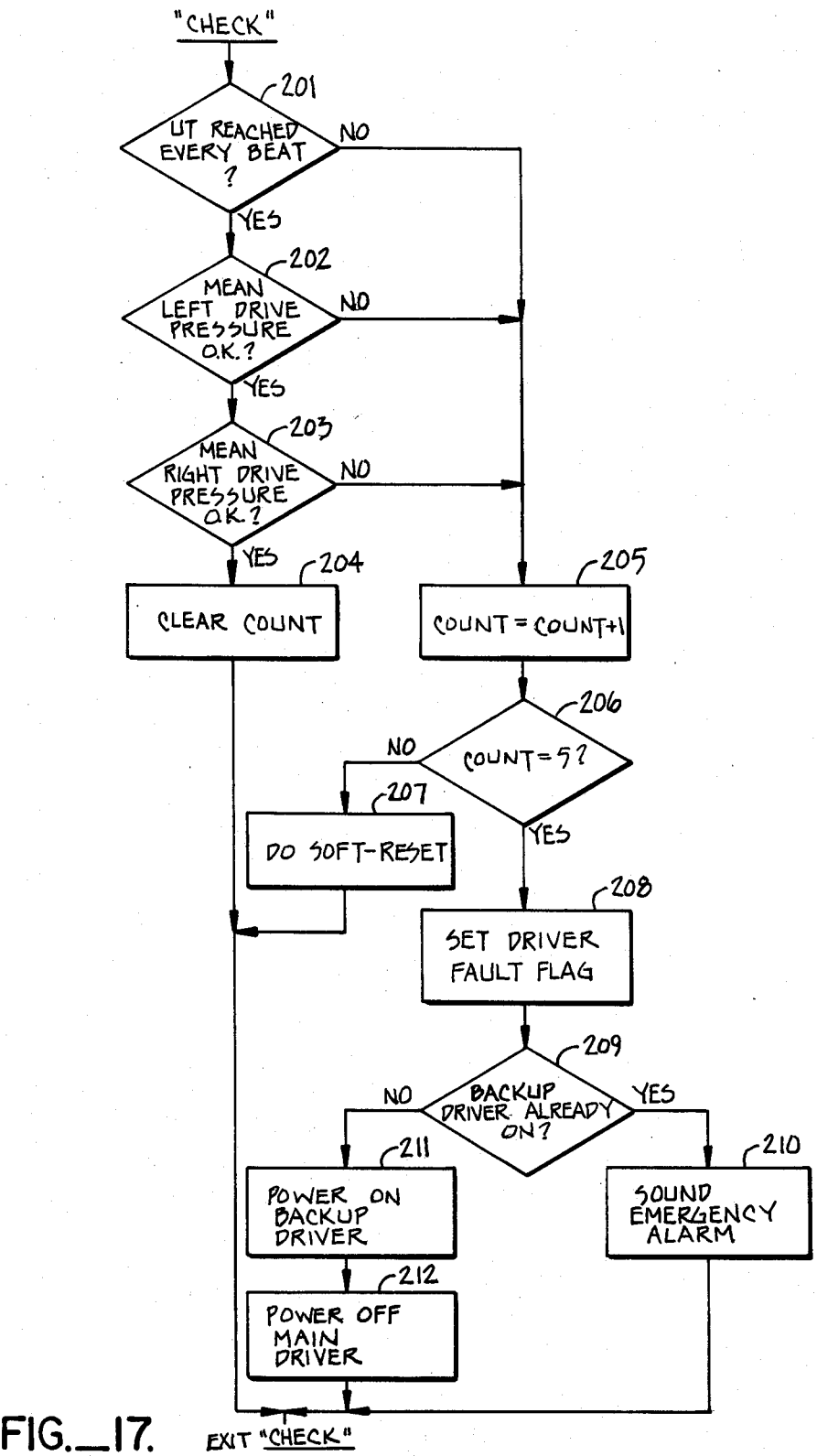
FIG._17.

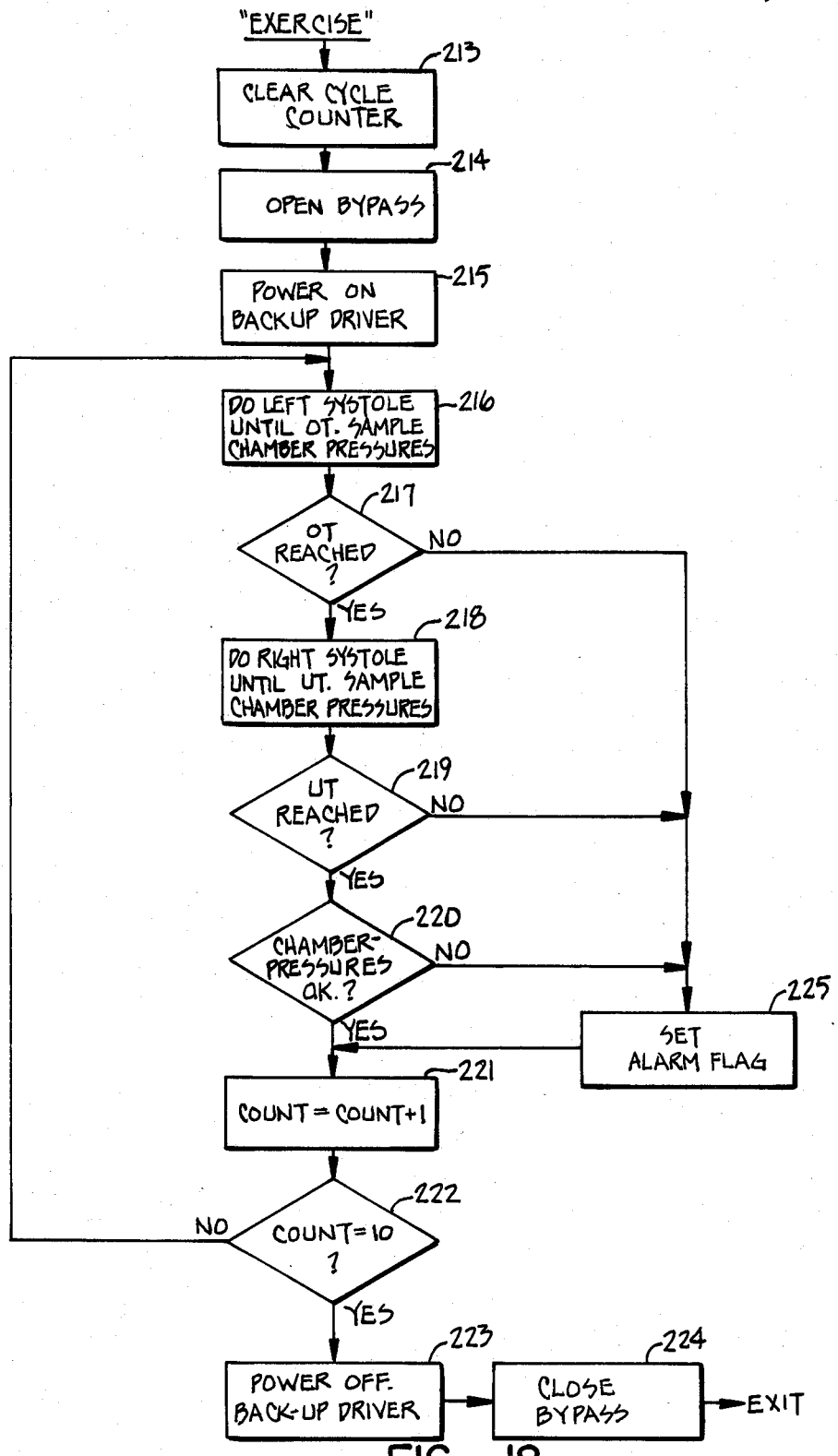
FIG._18.

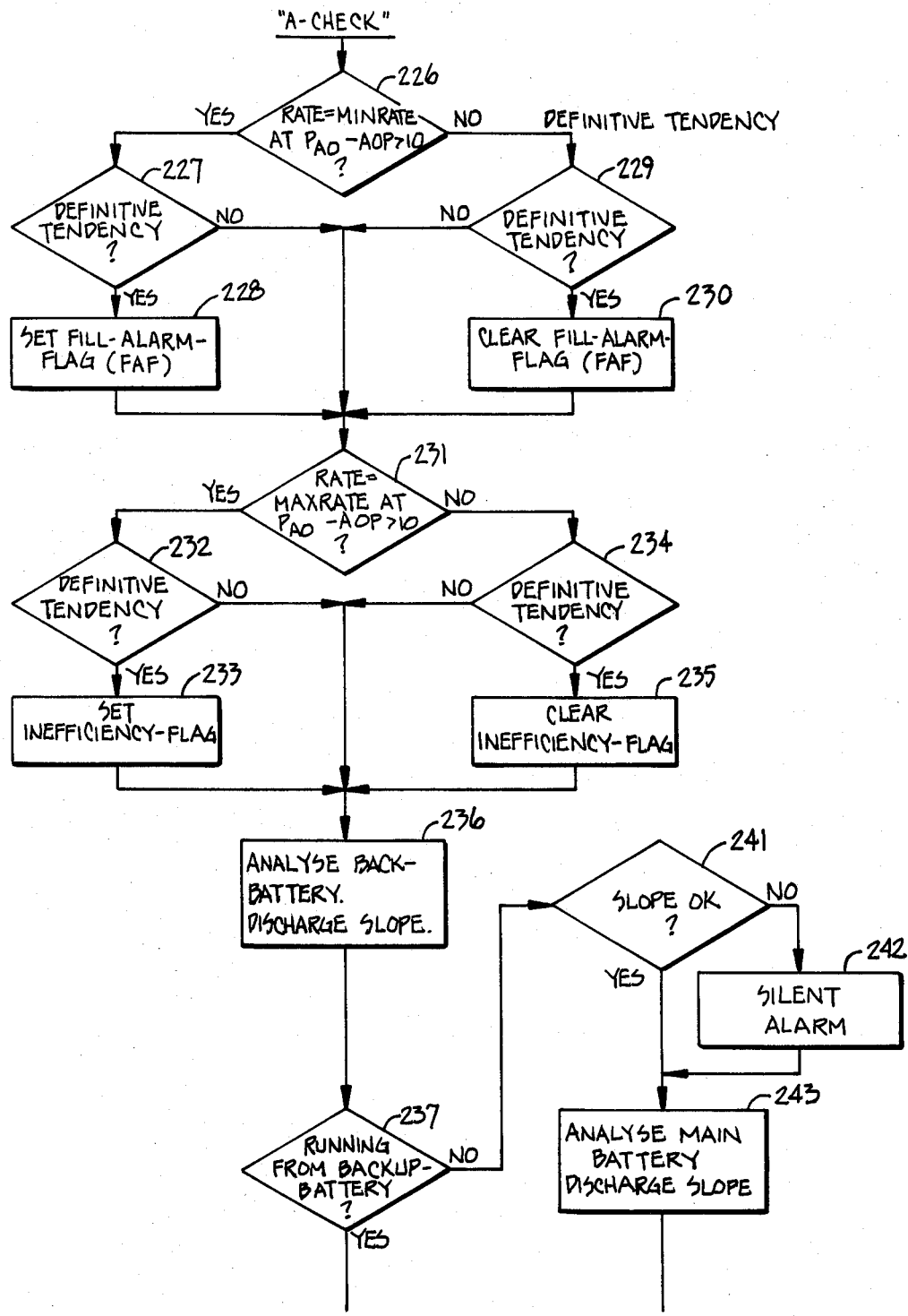
FIG._19A.

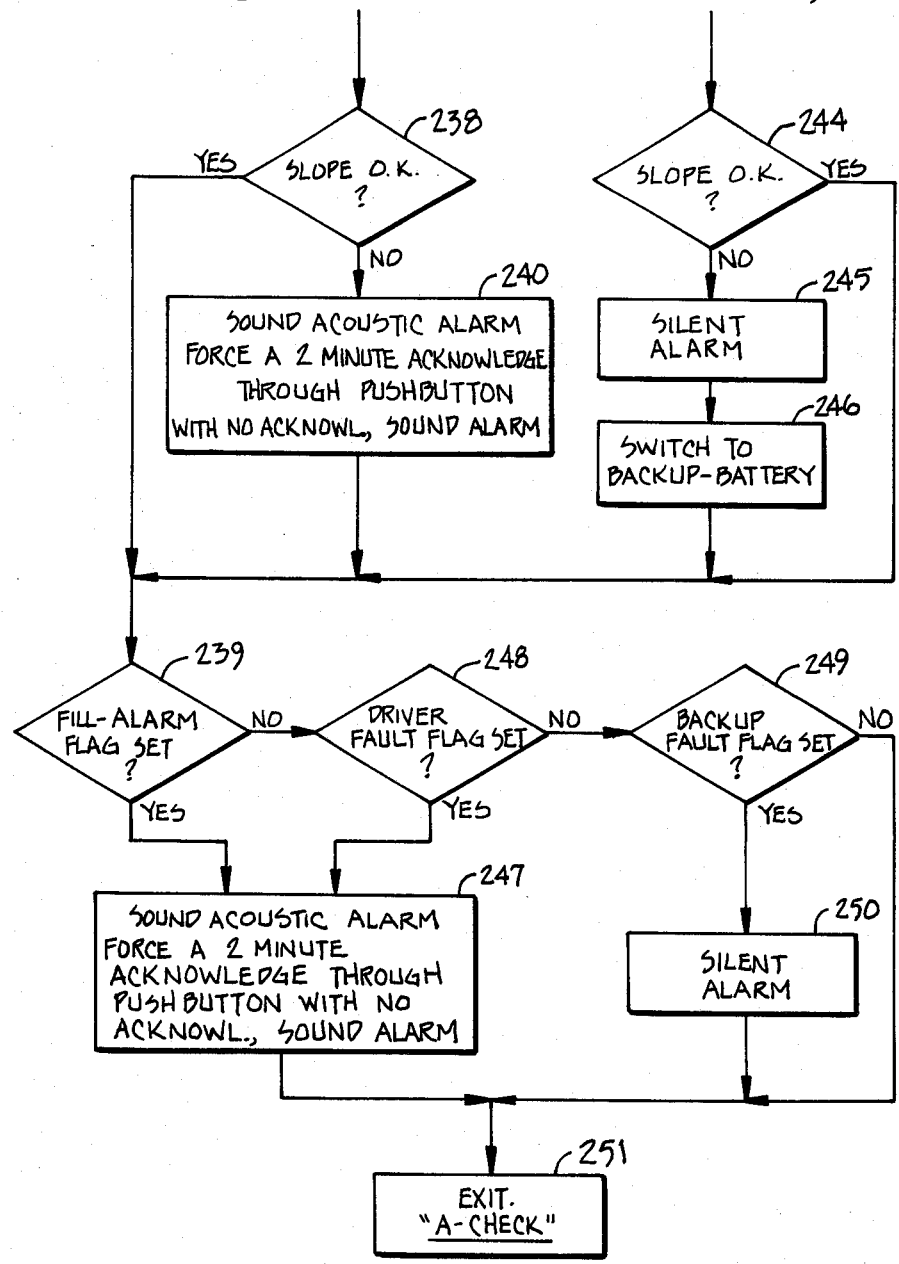
FIG._19B.

REDUNDANT PISTON PUMP FOR THE OPERATION OF SINGLE OR MULTIPLE CHAMBERED PNEUMATIC BLOOD PUMPS

DESCRIPTION

1. Technical Field

This invention relates to a blood pump and, more particularly, to a pneumatically driven blood pump.

2. Background Art

As illustrated in FIG. 1, a pneumatically driven blood pump consists of a relatively rigid spherical pump casing 112 which is subdivided by a thin, flexible diagraphm 111 into a blood chamber 113 and an air chamber 114. An inlet flap valve 115 and outlet flap valve 116 are installed in the pump casing on the side of the blood chamber. An air tube 43 connects the air chamber 114 to a chamber 42 within a cylinder 3 in which a slideable piston 1 is mounted. When the piston 1 is moved toward the tube 43, the air pressure is increased in the chamber 114 and exerts a pressure through the diaphragm 111 on the blood in the chamber 113, which has been completely filled through the inlet flap 115. If this pressure reaches the opening pressure of the outlet flap 116, the blood flows out through the completely opened flap 116.

If the piston 1 is now moved downwardly in the figure, the diaphragm moves in the opposite direction and flap 116 closes. The flap 115 then opens and new blood flows into the blood chamber 113 for the next pump's cycle. This cycle is repeated in accordance with the rhythm of the heart beat.

There are a number of inadequacies in the arrangement depicted in FIG. 1, particularly if two such blood pumps are to be used for the ventricles of a human heart. For example, if the piston were to fail, the patient in whose body the blood pumps had been installed would surely die. Yet, it is difficult to make a mechanical, pneumatic pump absolutely reliable and thus some redundancy is necessary. It is also necessary in the use of such blood pumps to take into account that the human body is not an ordinary plumbing system and that the blood pressure and blood flow rate must adapt to meet the body's needs. Because of problems of infections and other medical considerations, it is not considered entirely practical to implant sensor devices which could supply signals to a control system for the pump. Thus, some sort of system is required to non-invasively detect the body's circulatory requirements and to control the blood pump accordingly. Such a blood control system must be sensitive not only to the blood pressure within the circulatory system, but it also must be sensitive to the amount of blood volume flow through the heart. To simply increase the heart rate in order to meet some predetermined circulatory pressure may not be sufficient and may, in fact, even cause a condition known as circulus vitiosus, namely a constantly increasing heart rate with a steadily insufficient volume of blood flow through the heart.

Most importantly, particularly for use in powering a human mechanical heart, the system must be lightweight and portable.

DISCLOSURE OF THE INVENTION

The above and other advantages are achieved by the present invention of a piston pump for operating a chambered pneumatic blood pump, comprising a hollow cylinder which is closed at both ends, a pair of pistons slideably mounted within the cylinder, with the pistons and the interior walls of the cylinder defining a first chamber between the pistons and second and third chambers between the pistons and the ends of the cylinder, and means for selectively driving the pistons independently of, and in opposition to each other. A first pneumatic connection is provided between the first chamber of the blood pump and one of the first, second or third chambers of the piston pump. In the preferred embodiment of the invention, a second pneumatic connection is provided between a second chamber of the blood pump and another of the first, second or third chambers of the piston pump. In this embodiment, the blood pump consists of a pair of blood chambers and a pair of pneumatic chambers, constituting the mechanical ventricles for substitution in an actual heart.

First valve means are provided within the second pneumatic connection for selectively blocking access to either of the second or the third chambers of the piston pump. Second valve means are provided for selectively venting at least one of the chambers of the piston pump to the atmosphere while connecting the remaining chamber or chambers of the piston pump to the blood pump chamber or chambers. A mechanism is provided for holding stationary the piston which defines, in part, the second chamber while closing the first valve means to block access to the second chamber. The means for driving the pistons normally drives only a first one of the pistons unless there is a failure in which case the other piston is driven and the first piston is held stationary by the piston driving means.

In order to control the driving rate of the pistons, the piston driving means further includes means for sensing and calculating the volume of blood pumped by the blood pump during each stroke of the driven piston and for controlling the driving speed of said piston to maintain the predetermined volume of blood flow. The driving means further includes means for sensing and calculating the mean aortic pressure at the outlet of the blood pump and controls the driving speed of the piston driving means to maintain a predetermined mean aortic pressure at the outlet of the blood pump. The driving means further senses whether the blood volume pumped during each stroke of said driven piston falls below a predetermined value and thereafter blocks any increase in the rate of the piston driving speed. The driving means further senses the instantaneous air pressure within the cylinder and adjusts the stroke length of the driven piston as a function of said air pressure.

All such sensing of the stroke volume, the mean aortic pressure, and the air pressure is done non-invasively with sensors mounted only in the pneumatic pump itself and not within the patient in which the blood pump has been implanted.

Furthermore, the blood pump according to the invention is made of lightweight materials, is hand carryable, and contains its own power supply.

It is therefore an object of the present invention to provide a blood pump which has a redundant pneumatic driver.

It is yet another object of the invention to provide a portable driver for a blood pump.

It is yet a further object of the invention to provide a pneumatically driven blood pump which is instantaneously responsive to the circulatory system requirements of the human or animal in which the blood pump has been implanted.

It is yet a further object of the invention to provide a pneumatically driven blood pump which is non-invasively sensitive to the circulatory system requirements of the animal or human in which the blood pump has been implanted.

The foregoing and other objectives, features and advantages of the invention will be more readily understood upon consideration of the following detailed description of certain preferred embodiments of the invention, taken in conjunction with the accompanying drawings.

BRIEF DESCRIPTION OF THE DRAWINGS

FIG. 1 is a diagrammatic illustration of a prior art pneumatically driven blood pump;

FIG. 2 is a diagrammatic illustration of a redundantly implemented piston pump according to the invention, for the operation of a double chambered blood pump;

FIGS. 3, 4, and 5 are diagrammatic representations of the pneumatic pump illustrated in FIG. 2 together with safety valves, illustrating three different modes of operation;

FIG. 6 is a modification of the pneumatic pump according to the invention for the operation of a single chambered blood pump;

FIGS. 7, 8, and 9 are illustrations of the driving principles of a modified, redundantly implemented piston pump according to the invention, with control valves set in three different positions;

FIG. 10 is a vertical, sectional view, with portions depicted schematically, of the pneumatic pump according to the invention;

FIG. 11 is a block diagram of the mechanical pump depicted in FIG. 10 together with a control system therefor;

FIG. 12 is a block diagram illustrating the functions of a controller for the pneumatic pump depicted in FIG. 10;

FIG. 13 represents waveform diagrams for use in explaining the controller operation depicted in FIG. 12;

FIG. 14 is a diagrammatic, vertical, sectional view of a modified pneumatic pump according to the invention;

FIGS. 15A, 15B, and 15C, together, constitute a flowchart for use in explaining the operation of the pneumatic pump controller depicted in FIGS. 11 and 12;

FIG. 16 is a flowchart depicting a pump subroutine which is normally followed by the pneumatic pump controller;

FIG. 17 is a subroutine utilized by the controller for checking the operation of the main driver.

FIG. 18 is a subroutine utilized by the controller for checking the back-up driver for the blood pump; and FIGS. 19A and 19B are flowcharts for a subroutine used by the controller in checking the minimum and maximum heart rates in reference to the aortic pressure as well as for checking the main and back-up power supplies of the system.

BEST MODE FOR CARRYING OUT THE INVENTION

Referring now more particularly to FIG. 2, a pair of blood pumps 112 and 119 are pneumatically driven via the compression chambers 40 and 42 of a piston pump according to the invention. In this arrangement, a pair of pistons 1 and 2 are contained within a common cylinder 3 and are reciprocated by a drive means, which will be described further hereinafter. The pistons 1 and 2 can be driven synchronously in opposition to each other in normal operation or, as will also be explained in greater detail hereinafter, one of the pistons can be held rigid while the other piston is operated. If the operating piston fails, it can be held stationary and the previously stationary, back-up piston can then be operated to power the blood pumps 112 and 119.

The opposed faces of the pistons 1 and 2 together with the walls of the cylinder 3 define a first chamber 42. The backs of the pistons 1 and 2, together with the walls of the cylinder 3, define second and third chambers, collectively referenced as 40, which are connected together by a passageway 41. The chamber 42 is connected by means of a passage 43 with the air chamber 114 of the blood pump 112. The air chamber 40 is connected by means of the passageway 44 to the air chamber 118 of the blood pump 119. The blood pump 119 is constructed substantially identical to the blood pump 112 and has a diaphragm 111, a blood chamber 117, an inlet valve 122 and an outlet valve 123.

As is apparent from the illustration in FIG. 2, the blood pumps 112 and 119 operate in phase opposition. That is, during the compression of air in the left blood pump gas chamber 114, which occurs during the strokes when the pistons 1 and 2 are travelling towards the center, the blood pump 119 is undergoing decompression. The diaphragm 111 of the pump 112 is moving upwardly into the blood chamber while the diaphragm 111 of the pump 119 is moving downwardly to allow the blood chamber 117 to fill with blood. When the pistons are travelling away from each other, the reverse takes place and the chamber 113 of the pump 112 fills with blood while the blood chamber 117 of the pump 119 is placed under pressure from the diaphragm 111 to force blood out the valve 123.

The blood pump depicted in FIG. 2, with the addition of separate valves in the passageway 41, can selectively be operated in a number of different ways. Referring now more particularly to FIGS. 3, 4, and 5, it will be noted that, when the valves 51 and 52 in the passageway 41 are oriented to allow the end chambers 40 to be connected together to the outlet 44, as shown in FIG. 3, the blood pumps 112 and 119 are operated in opposition by the pistons 1 and 2 driven in opposition to each other. However, if the valve 52 is turned to the closed position and the piston 2 is held stationary, as shown in FIG. 4, the blood pumps 112 and 119 can still be operated by the reciprocation of the piston 1 all by itself. Furthermore, if the valve 51 is closed and the valve 52 is opened, then the piston 1 can be held stationary and the piston 1 can be reciprocated, as shown in FIG. 5.

The conditions depicted in FIGS. 4 and 5 can either be done selectively or, if need be, on an emergency basis. Thus, both pistons can be driven in opposition to each other until one of the pistons fails and then it can be held stationary and the appropriate valve 51 or 52 closed. In the preferred embodiment, however, one of the pistons is held stationary as a back-up for the other piston in case it fails. In the event that the active piston fails, it can immediately be held stationary and its associated valve closed. Thereupon the back-up piston can be activated and its valve opened. The purpose of having the valves 51 and 52 is to prevent the chamber 40 associated with the stationary piston from being dead space for the compression of the air volume.

Referring now more particularly to FIG. 6, a modification of the embodiment is depicted in which only a single blood pump 112 is powered by the pneumatic pump and the chambers 40 are vented to the atmosphere. A variation on this embodiment is depicted in FIG. 7 where the two blood pumps 112 and 119 can selectively be driven synchronously or in opposition. In this embodiment, a three way valve 120 is positioned to selectively interconnect the various passageways 41, 43, 44, and an externally vented passage 121. Furthermore, the air chamber 114 is connected directly to the left air chamber 40, associated with the piston 1. In the position shown in FIG. 7, reciprocation of either or both of the pistons 1 and 2 will cause the blood pumps 112 and 119 to operate synchronously. As the air is compressed in the chambers 40 by the pistons 1 and/or 2 travelling away from the center position, the blood in the chambers 117 and 113 is expelled from the blood pumps. As the pistons 1 and/or 2 travel to the center position, the blood chambers 113 and 117 fill with blood and the air chambers 114 and 118 are decompressed. The air in the chamber 42 is vented to the atmosphere through the valve 120 and the passageway 121.

When the valve 120 is rotated to the position shown in FIG. 8, the blood pumps 112 and 119 are operated in phase opposition by reciprocating either or both of the pistons 1 and 2. In the illustration, the piston 2 is held stationary and the piston 1 is reciprocated. When the air in the chamber 40 bounded by the piston 1 is compressed, blood is expelled from the pump 112. The pump 119 is decompressed and blood fills its blood chamber When the valve 120 is rotated to the position shown in FIG. 9, the blood pumps 112 and 119 again operate in phase opposition and either one of the pistons 1 and 2 can be operated while the other is held stationary. In this example, the piston 2 is reciprocated and the piston 1 is held stationary.

With reference now to FIGS. 10 and 11, the mechanical aspects of the pneumatic pump according to the invention will be explained. At the outset, it should be stated that there are numerous mechanisms for operating the pistons within in the pneumatic pump and while the applicant has found this particular embodiment to have many advantageous features, it should be understood that there are other suitable mechanisms which will be mentioned later in this description for powering the pistons.

As previously described, pistons 1 and 2 are mounted within sealing rings 4 and 5 in a common cylinder 3 and are situated at the left and right hand side of the pump as viewed in the figure. In this description, the reference numerals for common elements, symmetrically arranged on the left and right of the figure, will be stated together and it will be understood that they correspond to the duplicate mechanisms on the left and right side, respectively, of the pump.

The pistons 1 and 2 are rigidly connected to separate ball screws 8 and 9 through separate oscillation absorbers 6. The ball screws travel to and fro in separate ball screw nuts 10 and 11. The to and fro movement results from the change of direction of rotation of two separate motor rotors 12 and 13 in which the ball screw nuts are frictionally installed via separate vibration absorbers 14 and 15. The rotors are rotationally supported in ball bearing sets 16, 18 and 17, 19, respectively mounted in the stator assemblies of the motors 20 and 21. The rotors 12 and 13 are connected to separate optical coding discs 22 and 23, which face away from the pistons 1 and 2. Separate three phase windings 24 and 25 are situated in the stator assemblies of each of the rotors 20 and 21.

Each coding disc 22 and 23 is marked along its outer edge with marks or holes which are optically detected by separate light beam-photooptic sensor arrangements 26 and 27, respectively. The marks indicate the angular orientations of the coding discs relative to the sensors 26 and 27. Thus, by noting the starting point, the control system to be described in greater detail hereinafter can determine the relative position of the pistons by simply counting the number of markings detected by the sensors 26 and 27. Additionally, however, sensors 30 and 31 detect the outside limit of travel of the pistons 1 and 2 and sensors 28 and 29 detect the inside limit of travel of the pistons 1 and 2, respectively. These sensors can be light beam-photo sensors or any other type, such as Hall sensors, for example.

The coding discs 22 and 23 are not only used as position signals for the pistons 1 and 2, but they can also be used as position signals for the commutation of the stator windings 24 and 25 of the driving motors 20 and 21. In other embodiments, the coding discs 22 and 23 can be provided with coded screen marks which can be decoded instantaneously into the absolute position of the disc 22 or 23. Instead of light sensors, it is also possible to use discs with magnetic marks and magnetic sensors. Furthermore, although the motors in the preferred embodiment are electronically commutated direct current motors, in less advantageous embodiments the motors could be brush commutated direct current motors, step motors, or asynchronous or synchronous motors. The motors could even be linear motors.

The driving units are suspended in the common cylinder 3 by means of sound absorbing elements 32, 34, and 33, 35. Two end caps 36 and 37 are screwed onto the open ends of the cylinder 3 over sealing rings 38 and 39.

The spaces between the backs of the pistons 1 and 2 and the end caps 36 and 37 constitute the right and left outer gas chambers which are connected together via a channel 41 to make up a combined chamber 40. The combined gas chamber 40 is connected by means of the passageway 44 to the blood pump 119. The two piston faces, together with the middle section of cylinder 3, form the gas chamber 42 which is connected by passageway 43 to the left blood pump 112. Separate pressure relief valves 45 and 46 and separate air intake check valves 47 and 48 connect gas chambers 40 and 42, respectively, with the atmosphere.

In case of a breakdown of the active piston drive during a single piston operation, the defective piston drive is blocked by means of an electro-mechanical brake 49 or 50 and/or additionally by means of electric braking of the stator windings 24 and 25. At the same time, the connection of the passageway 41 to the left or right gas chambers 40 is blocked by means of the valves 51 or 52, as described above in reference to FIGS. 3, 4 and 5. As shown in FIGS. 10 and 11, the piston 2 is held stationary and blocked off from channel 44.

It will be noted that in the embodiment depicted in FIGS. 10 and 11, the blood pumps 112 and 119 operate in phase opposition. While this is not the normal operation of a human heart, it has been found to be perfectly satisfactory in terms of supplying sufficient circulatory blood pressure to a human patient whose actual heart ventricles have been replaced by artificial blood pumps.

Separate pressure sensors 53 and 54 are coupled to each gas chamber 42 and 40 to enable the electric measurement of the gas pressures for purposes of controlling the piston drives as will be described in greater detail hereinafter. The temperatures in the gas chambers are also measured by separate temperature sensors 64 and 65 which are mounted to sense the temperatures in chambers 40 and 42, respectively.

Referring now more particularly to FIG. 11, the pneumatic pump and the controls therefor are shown in block diagram fashion. The piston travel is controlled by an electronic driving circuit 62 which supplies driving signals to the motor stator windings 24 and 25 so that a rotating magnetic field having a given direction of rotation can be produced. Separate commutators 55 and 56 compare the instantaneous angular position of the respective rotors, determined by means of the coded discs 22 and 23 and the sensors 26 and 27 and supplies the stator windings 24 and 25 corresponding to this angular position with the necessary power from the power source 57. Power source 57 consists of portable, rechargeable batteries or a plug-in power supply, as the patient's situation dictates. Electronic commutation of such brushless DC motors is well understood and for this reason will not be described in greater detail. The stator windings are only supplied with the energy which is necessary to compensate for any speed deviations from nominal or reference speeds 58 or 59.

The actual rotational speed is taken from the rate of rotation of the coded discs 22 and 23. The order in which the stator windings 24 and 25 are successively connected to the power source 57 and, consequently, the direction of rotation of the rotating field of the motors, is determined by signals 60 and 61 from the control circuit 62. The control circuit 62 monitors the movement and the positions of both pistons 1 and 2 by means of the sensors 28, 30 and 29, 31 as well as the coding discs 22 and 23. The circuit 62 ensures that the piston operation meets certain predetermined standards for pressure output, rate, and in dual operation, that the pistons are operated synchronously If, for example, the circuit 62 detects a significant deviation of the stroke lengths of the pistons 1 and 2, during synchronous operation, which is recognized by means of the coded discs 22 and 23 or the signals from the limit sensors, synchronization is carried out by maintaining the faster of the two drives at the outer limit. If the attempt to synchronize the pistons cannot be achieved, the commutation of the drive deviating from the normal speed is stopped and the motor windings for that motor are short circuited. Furthermore, the corresponding brake 49 or 50 is activated. Since this is now an emergency, an alarm 63 is activated. Moreover, since a reduced piston stroke volume can be expected, the passive, dead volume of the stopped piston back represented by the chamber 40 is closed by the closing of the corresponding valve 51 or 52. Substantially the same sequence of events is carried out when operating with a single driven piston and a stationary back-up piston except that it is the previously active piston which is stopped and the back-up piston drive which is activated when the circuit 62 detects some malfunction with the operation of the first piston.

The circuit 62 receives reference information on the direction of rotation of the motor 109 and the nominal speed 110 from data entered by the operator of the device.

The control of the electro-pneumatic pump serves the purpose of adapting the pump automatically to changing circulatory system requirements of the patient and safeguards the right/left balance of the circulatory system. This latter property corresponds, on the average, to the desired identical output of the left and right artificial ventricles. The elements necessary for control purposes are the following:
1. Nominal value generators;
2. Actual value transmitters (e.g. sensors);
3. Servo components, including electro-pneumatic transducers, i.e. the motor drives and the pistons, and additional servo components;
4. The control unit which, in the preferred embodiment, is a microcomputer.

Referring now more particulary to FIGS. 11, 12 and 13, the operation of the control circuit 62 will be explained. The block "circuits" shown in FIG. 12 are actually functional operations carried out by a microcomputer acting as the controller 62. Controller 62 uses values measured exclusively outside of the human patient, that is it takes its measurements within the pneumatic drive. It does not rely on invasive measurement techniques nor does it rely on peripheral measurement techniques such as recording of bioelectronic signals. The sensory inputs to the controller 62 consist of the outputs from the pressure sensors 53 and 54 in the chambers 42 and 40, the piston position as measured by the coded discs 22 and 23 and the sensors 26 and 27, the air temperatures in the chambers 42 and 40 as measured by the sensors 65 and 64 and the atmospheric pressure as measured by a sensor 66. Further input values include the rates of pressure change, derived from differentiators 67 and 68 connected to the gas chamber pressure sensors 53 and 54. The stroke length 70 can be calculated by an absolute stroke calculator 69 from the position signals supplied by the coded disc sensors 26, 27, and the limit sensors 28, 29, 30, and 31.

The controller 62 begins from a reference starting heart rate, Fstart 71, which can normally be set between a lower reference rate, Fmin 73, and upper reference rate, Fmax 72, which are input to a frequency (heart rate) monitor 74 by an operator. This is the condition at the turn-on of the unit, when the piston or pistons 1 or 2 travel to and fro at a fixed frequency equal to the heart rate. This rate might be, for example, 80 beats per minute, but it can be adjusted to a different value. The values for Fmin and Fmax can, for instance, be between 40 to 180 beats per minute.

It should first be understood that blood pump 112 is primarily responsible for maintaining the circulation system requirements. In order to do this, the controller 62 is capable of operating the pistons 1 or 2 at one speed while the blood pump 112 is in the systole phase and at a second, usually slower, speed when it is in the diastole phase (in order to allow time for complete filling). The pistons 1 and 2 displace the driving air in the cylinder chambers 114 and 118, as described above, with the air chambers 114 and 118 being operated at 180° out of phase. Thus, when one chamber is being compressed, i.e. in the systole phase, the other chamber is being decompressed, i.e. it is in the diastole phase. Thus, increasing the diastole period of pump 112 necessarily increases the systole period for pump 119, in the embodiment shown in FIGS. 10, 11 and 12.

During systole, when the gas pressure within the chamber 114 or 118 reaches a pressure equal to the counter pressure at the outside of the outlet flap 116 or 123, the outlet flap opens and the blood in the blood pump is expelled. This results in a time/pressure function similar to the representation in the top portion of FIG. 13 which depicts the waveform signals from the pressure sensors 53 and 54 with respect to time.

The signals from the pressure sensors 53 and 54 are amplified by amplifiers 75 and 76 and are compared in comparator stages 77 and 78 with preset pressure values $P_{max}$ and $P_{min}$. The maximum and minimum pressures depend on the specific design of the equipment and the condition of the patient's circulatory system. At the exceeding of these limit values, the relief valves 46 and 45 are opened. This can be done electro-mechanically either in an active or in a passive way. When the valves 46 or 45 are opened, the pressure within the air chambers 114 or 118 is relieved. During the suction or diastole phase, the inlet valves 47, 48 (FIG. 11) open and allow the passive filling of the blood pump chambers.

The passive and active function of the relief valves is of particular significance for the balance of both blood pump volumes. The reason for this is that, if the blood chambers do not completely fill with blood during a suction cycle, the total air volume of the whole compression chamber consisting of the chamber 42, the channel 43, and the air chamber 114, for example, will increase. During the following systole phase, the blood pump diaphragm 111 will have stopped against the upper wall of the blood chamber 113 prior to the point when the piston 1 reaches the inside limit of its stroke. The gas pressure in the chamber 114 would then continue to increase until the piston reaches the inside limit position. However, because the valve 46 has been opened when the air pressure reached the Pmax value, the excessive pressure build-up within the air chamber 114 was prevented and, at the same time, the excessive air volume was released from the compression chamber. A similar operation takes place for the blood pump 119 through the valve 45.

This feature is a prerequisite to safeguarding the so-called "starling property" of the artificial ventricles. This property consists in that the instantaneously possible blood volume is a function of the filling pressure of the ventricles. For reasons concerning the circulatory physiology, this filling pressure-independent output guarantees the so-called "right/left-balance" within wide limits, depending on the charachteristic data of the blood pump chambers 113 and 117.

The instantaneous circulatory system requirement must be determined before the air pump system can be modified to match it. Two factors are considered by the control system, as mentioned above. The first is to determine the mean aortic blood pressure and the second is to determine how much blood volume is actually flowing through the blood pumps. Before the heart rate can be speeded up to compensate for a drop in the mean aortic pressure, the system must first check to determine that the blood pump flow is sufficient, otherwise a condition known as "circulus vitiosus" could occur in which a constantly increasing heart rate results in an insufficient beat volume due to bad filling of the blood pump during the diastole phase. If this condition were not accounted for, the total volume flow would continue to decrease and a sufficient blood pressure value could never be achieved.

The beat volume detection portion of the controller 62 determines the blood beat volume in a non-invasive way. The starting values for calculating the blood beat volume are the systolic driving gas pressures as indicated by the sensors 53 and 54 and the time history of the piston stroke 70. These waveforms appear at the top and bottom of FIG. 13. The output of the sensors 53 and 54 are supplied to differentiators 67, 68 which output the differentiated temporal pressure histories 93 and 94.

The beat volume calculators 82, 83 detect the characteristic points 97 and 98 of this curve, representing the opening and closing of the outlet flaps 116, 123 of the blood pumps 112 and 119. The absolute distance between these two points corresponds to a portion 99 of the total piston travel. This portion of the piston travel can be calculated by knowing the time between points 97 and 98 and the velocity of the pistons so that the actual distance travelled can be readily calculated. This distance is then multiplied by the effective piston surface 100, which value is previously known.

The thus determined stroke volumes represent the volumes of air utilized for the displacement of the blood situated behind the diaphragms 111 when the outlet flaps opened. These air volumes are equal to the blood beat volumes for the pumps 112 and 119 if they are corrected for various losses associated with the valves and for the fact that whereas blood is an incompressible fluid, air is compressible. This latter difference can be corrected by using standard gas equations for adiabatic changes in gas volumes if the pressures and temperatures are sampled from the sensors 53, 54, 64, 65, and 66. The valve losses due to fluid back flow through the valves on closing and due to a certain amount of continuous flow even after closing, as well as compliance losses due to such things as the elasticity of the blood pump casings can be modeled by empirical testing and stored in the controller's random access or programmed, read only memories (not specifically shown in FIG. 12, but understood to reside in the various functional blocks). All of these losses are pressure dependent and the back flow loss is also air flow rate dependent. Thus, these correction factors are stored along with the corresponding pressure and rate values.

The corrected stroke volumes are output from the beat volume calculators 82, 83 as signals 101, 102 to separate beat volume comparator circuits 84, 85 which will block a frequency increase from the output of the frequency (heart rate) monitoring unit 74, by means of an enable lead 92, if a comparison of the determined beat volumes with the stored characteristic volumes 95 and 96 of the blood pump chambers shows that the filling during the diastole phase was insufficient compared to these reference values.

If the frequency monitoring unit 74 determines such a state, i.e. insufficient beat volume, it will automatically begin to lower the driving frequency and, consequently, to prolongate the filling times for the blood pump chambers 113 and 117. If this produces no improvement, an alarm 63 is activated.

The determination of the mean aortic pressure 87 occurs in a waveform analysis unit 79 which monitors the pressure/time histories during a whole cycle at various piston positions as determined from the coding discs 22, 23, during a complete to and fro movement of the pistons 1 and 2. After completion of such a cycle, the waveform analysis unit 79 proceeds to analyze the amplified waveforms 88 and 89 of the left and right air chamber pressures together with the left pressure rise rate 93 at the known positions of the piston 1. This waveform analysis yields the blood chamber pressure at which the aortic outlet flap 116 is just opening.

This event is denoted as point 97 on the middle waveform in FIG. 13 and corresponds to the first point of most rapid pressure rise in the air chamber. This pressure would thus correspond more or less to the lower arterial blood pressure at the outside of the outlet flap 116. Point 98 corresponds to the closing of the flap 116.

The mean aortic pressure 87 is calculated at the heart rate set by the drive itself in a manner to be described in greater detail in reference to FIG. 15C, using the knowledge of the times and driving pressures when the valve 116 (or 123) opens and closes and stored correction factors 90. This calculated mean aortic pressure is compared in a pressure comparator 80 with a representative blood pressure reference value 81 ($P_{AO}$) If the actual value is below the nominal value $P_{AO}$, indicating too low an output or an increased circulatory system requirement, the frequency (heart rate) monitoring unit 74 outputs a signal 127 to the rotational frequency generator 86 which increases the heart rate by sending an increase in the frequency of the speed signal 58 (or 59) to the driving motor 20 (or 21).

If the reverse is true, namely that the mean aortic pressure is above $P_{AO}$, the heart rate is lowered by the unit 74 sending a decrease speed signal 128 to the rotational frequency generator 86 which lowers the frequency of the drive signal 58 (or 59) to the motor 20 (or 21). If the mean aortic pressure and the reference value $P_{AO}$ are substantially identical, the unit 74 maintains the current heart rate.

In any of the above cases, however, the unit 74 first checks whether the lowered or increased heart rate will fall within the Fmax and Fmin rates 72 and 73, respectively. It will also check to determine if the beat volume of the blood pump is sufficient by monitoring the enable signal 92. This signal represents the output at the beat volume detection system which was mentioned above.

The controller 62 can also control the length of the piston stroke to be travelled. In order to do this during dual piston operation, the length of the strokes of the two pistons 1 and 2 are first measured via an absolute stroke electronic system 69 by means of the coding discs 25 and 26. The strokes of each of the pistons are then compared with one another and, if the values deviate from one another, an alarm 63 is activated. For the most part, and in single piston operation, the strokes of the pistons 1 and 2 are only adjusted to compensate for deviations from the desired reference air pressures.

This is done by means of the window discriminators 77 and 78 which receive the amplified pressure sensor signals from the amplifiers 75 and 76 and then compare the pressure values during the whole cycle of the piston movement with the predetermined reference values $P_{max}$ and $P_{min}$. If the measured pressure exceeds $P_{max}$, the comparator 77 or 78 sends a signal 107 to a stroke calculator unit 104 to cause the stroke length to be decreased as long as the diaphragms 111 of the blood pumps 112 and 119 are just about reaching the upper full deflection, which is determined by noting where, during the entire length of stroke travel, the peak pressure occurs. At the same time, the comparators 77, 78 open the relief valves 45 or 46 in order to prevent damaging pressure peaks. If the pump diaphragms 111 do not reach the full deflection during the course of the stroke length, a signal 106 is sent by the comparators 77 or 78 to the unit 104 to cause the stroke 108 to be increased until the optimum position is reached.

A reference direction signal generator 109 supplies a direction reversal circuit 105 with a reference direction signal. The circuit analyzes the signals of the inside limit sensor 28 (or 29) and the outside limit sensor 30 (or 31) and decodes them by knowing the actual stroke direction into the instantaneously correct direction of rotation for the driving motor 20 (or 21).

Referring now more particularly to FIG. 14, a modified embodiment of the pneumatic pump is illustrated. An advantage of this design is that a failure of the seals around the active piston will not render the entire pump defective which could conceivably happen with the pump design illustrated in FIG. 2. In this embodiment, the piston 2 is normally held stationary as a redundant, back-up pump and the piston 1 is reciprocated. The modifications to the pump in the form depicted in FIG. 2 consist in that a septum 129 divides the chamber 42 in half and extends up into the passageway 43 to mate with a bidirectional valve 133. Depending on the position of the valve 133, it can connect the passageway 43 with either the left hand portion of the chamber 42 (piston 1) or the right hand portion of the chamber 42 (piston 2) as viewed in FIG. 14. An additional modification is an upstanding flange 136 in the passageway 41 where it mates with the passageway 44. This flange 136 seals with a bidirectional valve 134 which, depending on its position, can connect the passageway 44 either with the channel 41 (piston 1) or with the chamber 40 bounded by the piston 2 and the cylinder 3.

The valves 133 and 134 are connected to operate together by a connecting rod 135 activated by a suitable electro-mechanical device (not shown) operated by the controller 62. Additional pressure sensors 53' and 54' are installed in the housing to read the pressures in the chambers 42 and 40, respectively. These sensors are to be used, as will be explained later in this description, to test the redundant driver.

In the position of the valves 133 and 134 shown in FIG. 14, the blood pumps 112 and 119 are normally driven in phase opposition by the reciprocation of the piston 1 in the manner described in reference to FIG. 4. If the piston 1 should fail for any reason, the control unit 62 will reposition the valves 133 and 134 to the second of the two positions so that the blood pumps 112 and 119 will be driven by the piston 2. At that point, the operation of the system will be substantially the same as that described in reference to FIG. 5, except that the redundant driver will be completely cut off from the faulty driver by the septum 129 and the valves 133 and 134.

During normal operation, when the piston 2 is held stationary, it is occasionally desirable to check the operation of the back-up driver by activating it. Of course, during such testing periods, the air pressure produced by the operation of the piston 2 must not be allowed to reach the blood pumps. In order to provide such a testing capability, a passage 130 connects the chamber 40 on the back side of the piston 2 with the chamber 42 on the face side of the piston. A by-pass valve 131 positioned in the passageway 130 and a restrictor 132, also placed in the passage 130, allow for control during this exercise. In order to test the piston 2, the valve 131 is rotated to be open in the passage 130 and the amount of air pressure built up in either the chamber 42 or the chamber 40 is relieved through the restrictor 132 to thereby allow the seals around the piston to be checked and also to provide for a dummy load in simulation of the blood pump.

Referring now more particularly to FIGS. 15A and 15B, these figures, as well as the figures to follow, depict the flow chart of operations of the controller 62. As previously mentioned, the controller 62 is a programmed microcomputer and all of the various block elements depicted in FIG. 12 actually correspond to operations of the microcomputer, although, in other embodiments, these same functions could be carried out by hardwired logic.

The first step 137 taken by the microcomputer 62 is to do a cold initialization in which the heart rate is set arbitrarily to a predetermined rate Fstart 71, which is, in this example, taken at 70 beats per minute. Next, the percent systole left stroke volume is set equal to 80% of the full available volume, i.e. a predetermined start stroke length is chosen to pump 80% of the available volume during the systole phase of the blood pump 112. Finally, the left systole is set to a predetermined "start" percentage of the total piston stroke, i.e. the controller instructs the motor 20 (or 21) to move the piston at a speed during systole (for the pump 112) which will cause the pump to spend the desired percentage of the total cycle in systole. The start-up-count is also set.

The controller 62 next powers up the driver at step 138 by supplying power from the source 57 to the commutator 55 as well as to the other electromechanical servo elements. At step 139, the interrupt routine PUMP is enabled.

An inquiry is made at step 140 as to whether the controller 62 is operating in the start-up condition. If the answer is yes, the controller 62 will check for correct driver operation by continuing to run the CHECK subroutine program at step 141 until the start-up condition has passed. Both the PUMP and the CHECK subroutines will be explained in greater detail hereinafter, however, for the present purpose it is sufficient to state that the PUMP subroutine commutates the motor 20 (or 21) with the predetermined systolic speed and the predetermined diastolic speed and with the predetermined direction as is computed by the main program of the controller 62 to meet the circulatory pressure system requirements. The CHECK subroutine makes sure that the left and right drive pressures (derived by scanning the sensors 53, 54) are sufficient and that the outside limit (determined from the sensor 30) is reached by the driving piston on every stroke. In the event that these conditions are not satisfied, the CHECK subroutine will activate the back-up driver.

After completion of the start-up condition, the controller 62 next calculates updated systolic and diastolic motor speeds and stroke length parameters at step 142. This corresponds to the operations of the frequency monitor 74 and the stroke calculator 104 discussed in reference to FIG. 12. These values will be implemented in the PUMP subroutine.

In the next series of steps 143-151, the beat volume function 82 of FIG. 12 is carried out. At step 143, the air pressure supplied to the left blood pump 112 is analyzed by means of the output of the sensor 53 to determine the air pressure at the point when the aortic valve opens ($P_{oav}$), the air pressure when the aortic valve closes ($P_{cav}$), the time when the aortic valve opens ($T_{oav}$) and the time when the aortic valves closes ($T_{cav}$). All of these values can be determined by monitoring the output of the differentiator 67 to note the pressures and the points in time 97, 98 (FIG. 13) when the pressure rise within the chamber is at its maximum rate of change.

Proceeding on to step 144, the controller 62 calculates the systolic volume, "SVL" as being equal to the active piston area 100 (FIG. 12) times the distance travelled by the piston between the time $T_{oav}$ when the aortic valve opens and the time $T_{cav}$ when the aortic valve closes. This calculated volume must be compensated for the difference in pressure which is experienced by that volume during the compression cycle, due to the fact that air is a compressible medium whereas blood is not. This is done by setting the systolic volume (SVL) equal to the product of the previous calculated value for "SVL" times the ratio of $(P_{cav}/P_{oav})^K$ where K is an empirically determined constant. The value K is stored in look up tables in memory and is accessed. Like all of the constants which will be mentioned in this description, K is derived from a mock test set up using blood pumps, drive lines and drivers of the same design and by carefully measuring the actual air volume, the stroke length, the air pressure and the heart rate. It will be apparent that for these known factors the constant K is defined by:

$$K = \frac{\log \frac{SVL}{SVL'}}{\log \frac{P_{cav}}{P_{aov}}}$$

where SVL'=(active piston area)×(stroke length). It has been determined that SVL has a constant, but heart beat dependent relationship with SVL'. This allows a look-up table to be compiled giving K as a function of $P_{cav}$, $P_{aov}$, the stroke length and the heart beat rate.

In the next sequence of steps 145 through 148, inclusive, the computer determines three different constants KL1, KL2 and KL3 to compensate for valve losses as a function of the pressure, valve losses as a function of the active air flow, and compliance losses due to the change in pressure. These losses were previously discussed in detail in regard to the functional block 82 in FIG. 12. At step 149, the blood systolic volume, BSVL is set equal to SVL times KL1 times KL2 times KL3.

Basically, the first two of these losses are derived from mock test set-ups using water-glycerol mixtures to simulate the newtonic viscosity of blood in the blood pump 112. KL1 actually represents a constant which is derived from a look-up table in memory as a function of the pressure sensed from sensor 53 and by knowing the heart beat rate. The data for the look-up table is generated using the mock test set-up at different heart beat rates between 60 and 130 beats per minute with a constant ejection time and a constant stroke volume. This table therefore contains correction factors which represent the regurgitation for the particular type of valve 116 which is used and the position in which the valve is mounted in the individual blood pump 112. The test load on the blood pump, representing the aortic pressure, is also set to 95 mm. Hg.

The second correction factor KL2 again represents data in a look-up table. The active airflow is the input parameter to the look-up table. The active airflow, of course, is calculated by knowing the stroke volume calculated in step 144 which occurs between $T_{cav}$ and $T_{oav}$, as determined in step 146 of the controller program. In a mock test set-up experiment, the actual stroke volume (blood) is compared with a constant air stroke volume for different active airflow values between 2 and 5 liters per minute against a constant mean aortic pressure of 95 mm. Hg. and with complete filling. The numbers in the table represent percentages of the blood displacement volume for these figures.

The correction factor KL3 is static. It represents compliance loss factors which, again, are stored in a look-up table and which are derived from a different mock test set-up from the one used for deriving constants KL1 and KL2. In this mock test set-up, the outflow valve 116 is sealed and the inflow valve 115 is replaced with a tube in which water is used to pressurize the blood pump 112. The measured pressure-volume relation is then put into a look-up table. It must be understood that all of the constants KL1, KL2 and KL3 will vary depending on the particular blood pumps or valves which are used as well as changes in the design of the driver.

In step 150, the controller retrieves a reference stroke volume at the current heart rate from memory, and assigns this value to the variable CSVL. At step 151, the controller 62 determines whether or not the calculated BSVL is less than the CSVL reference. If the answer is no, indicating that sufficient blood volume is being produced, the controller 62 sets an enable rate increase flag at step 152. This corresponds to the enable signal 92 depicted in FIG. 12. If the blood stroke volume is less than the reference volume CSVL, then an "increase percent diastole left" flag is set at step 156 and the controller 62 proceeds to analyze the air pressure in the right blood pump 119.

The sequence of steps 154–162 corresponds to the beat volume calculator 83 of FIG. 12. In steps 154 through 162, the controller 62 proceeds in the same manner as described above in reference to steps 143 through 151 to determine whether or not the blood stroke volume for the right blood pump 119 is greater or less than a reference volume for the same heart rate. If at step 162 the answer is determined that it is not, then a rate increase enable signal is generated at step 163, which, as previously explained, corresponds to the signal 92 in FIG. 12. If, on the other hand, the blood stroke volume is insufficient compared to the reference CSVR, then an "increase percent diastole right" flag is set at step 164.

After thus determining whether the blood stroke volumes are sufficient, the controller proceeds to set the heart rate, corresponding to the function 74 in FIG. 12. Since the pumps 112 and 119 operate in opposition, increasing the diastole of one pump shortens the diastole of the other pump unless the heart rate is also decreased. At step 165, the controller 62 makes a determination of whether both the left and the right blood pumps 112, 119 require an increase in the percent diastole, i.e. whether the controller needs to allow both blood pumps more time to fill with blood. If the answer is no, a rate increase enable flag is set at step 163. If, on the other hand, both blood pumps demand an increase in the percent diastole, a decrease rate flag is set at step 166 and a disable rate increase flag is set at step 167.

If the controller 62 determines at step 168 that the heart rate has now reached the minimum rate, then an alarm is sounded at step 169 corresponding to alarm 63 activated by the frequency monitoring function 74 in FIG. 12. If the minumum rate has not been reached, then the mean aortic pressure is calculated at step 170 from the values for the pressure at the opening of the aortic valve, the pressure at the closing of the aortic valve, Pcase, and the time difference between the opening and the closing of the aortic valve. This corresponds to the operation carried out in the waveform analysis logic 79 described above in reference to FIG. 12. Pcase is the pressure occurring at the minimum in the middle pressure waveform at FIG. 13, between the opening and the closing of the aortic valve. The mean aortic pressure can be calculated by multiplying Pcase by an empirically determined constant which is characteristic of the blood pump housing and by adding to this product a second empirically determined constant.

As in the determination of the valve losses, these constants are derived using a mock test set-up having a known outlet back pressure and then sampling $P_{oav}$ and $P_{cav}$ at different heart rates (i.e. different values of $T_{cav} - T_{oav}$). These samples are plotted as a function of Pcase to yield a relationship:

$$\text{mean AOP} = A(\text{Pcase}) + B$$

where A and B are the empirically determined constants which are stored in a look-up table.

Alternatively, if Pcase cannot be readily determined, mean AOP can be approximated using $P_{oav}$ and $P_{cav}$. The mean AOP is calculated between those two air pressures by the formula $\frac{1}{3}(P_{oav} - P_{cav}) + P_{cav}$. For example, for 120 mm. Hg./80 mm. Hg. we get a mean AOP of 93.3 mm.Hg.

If, at step 171, the controller 62 determines that the calculated mean aortic pressure is less than the reference pressure $P_{AO}$, corresponding to the functional block 80 of the FIG. 12 diagram, the controller will next determine at step 172 whether a rate increase disable flag has been set. If it has, it will leave the rate unchanged 173. If no rate increase disable flag has been set, then the rate will be increased at step 174, corresponding to signal 127 in FIG. 12.

If, at step 171, the mean aortic pressure is determined to be equal to $P_{AO}$, the rate will be left unchanged at step 173. If the determination at step 171 is that the mean aortic pressure is greater than $P_{AO}$, the controller 62 will determine whether the minimum rate has been reached at step 175 and if not, the rate will be decreased at step 176, corresponding to signal 128 in FIG. 12. If the minimum rate has been reached, the rate will be left unchanged at step 173.

After the mean aortic pressure has been compared to $P_{AO}$, the end systolic pressure peak is located at step 177 by analyzing the pressure waveform. This is done for both the right and left pressure sensors 53 and 54 and corresponds to the functional blocks 77 and 78 of FIG. 12. This pressure peak is shown as point 98 in the waveform depicted in FIG. 13 and reflects the fact that the diaphragm 111 has been pressed against the upper wall of the blood pump chamber.

At step 178, the controller 62 determines whether or not this peak occurred at 90% of the overall stroke length. If the determination is that the peak occurs before this point, the stroke length is decreased at step 179. If it does occur at this point, the stroke length is kept constant at step 180. If the peak occurs after this point, the stroke length is increased at step 181. These operations correspond to the stroke calculator function 104 of FIG. 12.

The controller then proceeds to update the cycle counter, step 182, and to determine at step 183 if the cycle count has reached a predetermined integer N which represents how often the back-up driver is to be tested. If the answer is yes, the controller next determines if the back-up driver is already on at step 184. If the answer is no, the controller 62 runs the "EXERCISE" subroutine to test the redundant driver at step 185. Had the determination at step 183 been negative, or had it been positive at step 184, the EXERCISE subroutine would have been skipped over.

After step 185, the controller does an analysis of the alarm state by running the "A-CHECK" subroutine at step 186, and finally checks for correct driver operation by running the "CHECK" subroutine at step 187. After the completion of the CHECK subroutine at step 187, the controller returns to step 142 to repeat the sequence of operations described above.

Referring now more particularly to FIG. 16, the PUMP subroutine which is implemented at step 139 in FIG. 15A will now be described. As set forth in the statement at step 189, the pump objectives are to commutate the speed of the motors 20 and 21 with the systolic speed, the diastolic speed and the direction calculated at step 142 in FIG. 15A. It should be noted that the speed of the motors in stroking the pistons 1 or 2 in one direction may not be the same as the speed of stroking the pistons in the opposite direction. In this context, since the blood pumps 112 and 119 are normally in phase opposition, the terms systolic and diastolic are used in this PUMP subroutine program to refer to the left blood pump 112 which is primarily responsible for maintaining the blood pressure in the circulatory system.

In the first step 190 of this subroutine, the proper direction of rotation of the motor 20 (or 21) is determined by the microcomputer based on the initial direction reference signal 109, the coded disc sensor 26 (or 27), and the signals from the inside and outside limit sensors 28 (or 29), 30 (or 31), as explained above in reference to FIG. 12. At step 191, the speed necessary to maintain the desired stroke rate calculated at steps 173, 174 or 176 in FIG. 15C is supplied to the commutation circuit 55 (or 56) as described above in reference to FIG. 11. At step 192, the controller 62 samples the left drive pressure signal from the sensor 53, the right drive pressure signal from the sensor 54, and stores these signals in random access memory along with the instantaneous piston position at the time the pressure was sampled. This corresponds to the waveform analysis logic function 79 described above in reference to FIG. 12 and is the data needed for steps 143 and 154 in FIG. 15A.

A pointer in the random access memory is incremented at step 193 and a determination is made at step 194 whether the end of the stroke has been reached. Whether or not this has happened is determined by either sensing the outside limit sensor 30 (or 31), or by calculating the distance the piston has travelled by counting the revolutions of the coding disc 22 (or 23) with the sensor 26 (or 27). Of course, the absolute limit for the stroke can also be determined by the inside stroke limit sensor 28 (or 29) in the event that a full stroke has been ordered.

If the set stroke has not been reached, the program returns to step 190 and repeats itself. If the end of the stroke has been reached, the controller 62 determines whether the end of the diastole period has been reached. If not, the change direction flag is set at step 196 and the program is begun again at step 190. If, on the other hand, the end of the diastole period has been reached at step 195, the table pointer for indexing the random access memory is reset at step 197, a start-up counter is counted down at step 198 and a determination is made whether or not the start-up period has ended at step 199. If the answer is yes, the start-up flag is cleared at step 200, the direction flag is changed at step 196, and the program is begun again at step 190. If the answer at step 199 is no, the direction flag is changed at step 196 and the program is begun again at step 190.

Referring now more particularly to FIG. 17, in the CHECK subroutine, the controller 62 at step 201 first scans the outside limit sensor 30 (or 31) to make sure that the active piston has reached the full limit of outside travel on every beat. Assuming that it has, the next step 202 determines whether the mean left drive pressure falls within $P_{max}$ or $P_{min}$ as explained above in reference to function 77 in FIG. 12. This is done, of course, by scanning the output of the left pressure sensor 53. Assuming the answer is yes, the controller 62 proceeds to step 203 where it similarly determines whether the mean right drive pressure falls within $P_{max}$ and $P_{min}$, corresponding to the function 78 in FIG. 12. If the answer is yes, at step 204 a counter is cleared and the subroutine is exited.

If any one of the preceding tests at steps 201, 202, or 203 resulted in a negative, the counter will be incremented by one at step 205 and, at step 206, the controller will look to see whether the counter has counted up to five. If not, a soft reset function will be performed wherein the initial values at step 137 are reimplemented and the pump routine is re-enabled. Naturally, the check subroutine will again be run at step 141. In doing the soft reset, however, the count in the counter will not be cleared.

If the determination made at step 206 is that the count equals 5, a driver fault flag is set at step 208 and a determination is made as to whether or not the back-up driver is already on at step 209. If it is, then at step 210 an emergency alarm is sounded since this means that not only the main piston drive but also the back-up piston drive are not operating correctly. If the answer at step 209 is a negative, the controller 62 will then power on the back-up driver at step 211 and turn the main driver off at step 212 and will exit the subroutine.

Referring now more particularly to FIG. 18, the EXERCISE subroutine is illustrated wherein the redundant piston and driver can be checked. At step 213, the controller clears the cycle counter (FIG. 15C) and then opens the by-pass valve 131 (FIG. 14). At step 215, the back-up driver is powered on.

The blood pump 112 is operated at step 216 in systole, that is compression, until the inside limit sensor 29 determines that the piston 2 has travelled as far to the left as it can, as viewed in FIG. 14. The pressures of chambers 42 and 40 are then read from pressure sensors 53' and 54'. If there is no output from inside sensor 29, as determined at step 217, the program proceeds to step 225; the setting of an alarm flag. If there is an output at step 217, the controller puts the right blood pump 119 into systole until the outside limit sensor 31 registers an output at step 218. At that point, the pressures in the chambers 42 and 40 are again sampled by means of the sensors 53' and 54'. If the outside limit is not reached at step 219, the alarm flag is set at step 225. If the limit is reached, then the chamber pressures are compared to predetermined reference chamber pressures at step 220. Again, if a failure is noted, an alarm is set at step 225. If no failure is noted, the count in the counter is incremented by one, step 221, and the controller looks to see if it has reached 10, step 222. If not, the program repeats, beginning at step 216.

Once a count of 10 is reached, the back-up driver is powered off, step 223, the by-pass valve 131 is closed at step 224 and the program is exited.

Referring now more particularly to FIGS. 19A and 19B, the A-CHECK subroutine will be described. In the first step, 226, the controller determines whether or not, when the difference between the reference pressure $P_{AO}$ and the mean aortic pressure is greater than 10, the heart rate is equal to the minimum rate (Fmin, 73 in FIG. 12). This would indicate that the mean aortic pressure is less than it should be and that the heart rate cannot be lowered any further. If the answer at step 226 is yes, the controller looks to see if there is a definitive tendency toward this condition. This is determined by taking a number of samplings over a predetermined time period and observing whether the average of these points is tending toward or away from the noted condition. If the answer at step 227 is yes, the fill alarm flag is set at step 228. If the answer is no, the routine proceeds to step 231.

If at step 226 the answer was no, indicating that the minimum rate had not yet been reached, the controller 62 again makes a determination of whether this constitutes a definitive tendency at step 229. If the answer is no, the routine proceeds to step 231. If the answer is yes, indicating that, while the mean aortic pressure is below what it should be, the minimum rate has not yet been reached, the fill alarm flag is cleared at step 230.

At step 231, a second rate check is made. In this test, when the difference between the reference pressure $P_{AO}$ and the mean aortic pressure is greater than 10, the controller looks to see whether the heart rate is equal to the maximum rate (Fmax, 72, in FIG. 12). If the answer is yes and a definitive tendency is indicated at step 232, an inefficiency flag is set at step 233. This could happen for physiological reasons or even if, for example, one of the valves 47 or 48 was not operating properly or the seals around the piston 1 were leaking. If the answer is no, the program proceeds to step 236.

If, at step 231, it was determined that the maximum rate had not yet been reached, and a definitive tendency for this was not shown at step 234, the program again proceeds to step 236. If there is a definitive tendency shown in step 234, then the inefficiency flag is cleared at step 235, and the program proceeds to step 236.

The next sequence of steps is intended to confirm that the power supplies for the main driver and the back-up driver are in correct operating condition. First, the discharge slope of the back-up battery is analyzed at step 236. The question is then asked at step 237 whether or not the driver is being powered from the back-up battery. If the answer is yes, and the slope is confirmed as being correct at step 238, the program proceeds to step 239. If the slope is not all right, an acoustic alarm is sounded at step 240 which requires a two minute acknowledgement by means of a push button. If there is no acknowledgement, a second alarm is sounded and the program proceeds to step 239.

If at step 237 it was determined that the driver was not being powered by the back-up battery, the program nevertheless determines if the slope of the back-up battery is OK at step 241. If it is, step 243 is implemented. If it is not, a silent alarm is activated at step 242.

After steps 241 or 242, the program proceeds to analyze the discharge slope of the main battery at step 243. If, at step 244, the slope is determined to be all right, the program proceeds directly to step 239. If, on the other hand, the slope is not all right, a silent alarm is activated at step 245 and the main power is turned off and the back-up battery is turned on at step 246.

Proceeding on to step 239, the controller checks to see whether the fill alarm flag has been set. It will be recalled that this flag would have been set at step 169 in FIG. 15C. If the answer is yes, an acoustical alarm is sounded at step 247 which requires a two minute acknowledgement by activation of a push button with an alarm being sounded if no acknowledgement is received within the two minute period. If no alarm flag has been set, the controller next checks, at step 248, to see whether a driver fault flag has been set. Such a flag would have been set at step 208 in FIG. 17. If the answer is yes, the controller proceeds to step 247 and the sounding of the alarm. If the answer is no, the controller next checks, at step 248, whether the back-up fault flag has been set. The back-up fault flag would have been set at step 225 in FIG. 18. If the answer is no, the program exits the A-CHECK subroutine. If the answer is yes, a silent alarm 250 is activated.

While in the above described embodiment the control functions are implemented in the software of a microcomputer for reasons of flexibility, it will be understood that these same functions could be carried out in hardwired circuitry or "firmware" in other embodiments, particularly where reliability, low manufacturing costs and small size are of paramount importance.

The terms and expressions which have been employed here are used as terms of description and not of limitations, and there is no intention, in the use of such terms and expressions, of excluding equivalents of the features shown and described, or portions thereof, it being recognized that various modifications are possible within the scope of the invention claimed.

I claim:

1. A piston pump for operating a chambered pneumatic blood pump comprising: ends,
    a hollow cylinder which is closed at both ends,
    a pair of pistons slidably mounted within the cylinder, said pistons and the interior wall of said cylinder defining a first chamber between the pistons and second and third chambers between the pistons and the ends of the cylinder,
    means for driving the pistons independently of, and in opposition to each other, and comprising means for sensing and calculating the volume of blood pumped by the blood pump during each stroke of at least one of said pistons and for controlling the driving speed of said piston to maintain a predetermined volume of blood flow, and
    a first pneumatic connection between first chamber of the blood pump and one of said first, second or third chambers of the piston pump.

2. A piston pump as recited in claim 1 wherein the driving means comprises means for sensing and calculating the mean aortic pressure at the outlet of the blood pump and for controlling the driving speed of the piston driving means to maintain a predetermined mean aortic pressure at the outlet of the blood pump.

3. A piston pump as recited in claim 2 wherein the driving means senses and calculates whether the blood volume pumped during each stroke of said one piston falls below a predetermined value and for thereafter blocking any increase in the rate of the piston driving speed.

4. A piston pump as recited in claim 1 wherein the driving means further includes means for sensing the gas pressure produced while only the first one of said pistons is driven and means for comparing the sensed pressures with predetermined reference standards to determine if the driven piston has failed to produce pressures equal to such reference pressures.

5. A piston pump for operating a chambered, pneumatic blood pump, in a patient, comprising
    a pump casing having piston chambers,
    a pair of pistons slidably mounted within the chambers in the casing, means for selectively driving the pistons independently of each other, a pneumatic connection between a chamber of the blood pump and one of the piston chambers of the piston pump, and a controller for the piston driving means which controls the stroke lengths and rates of reciprocation of said pistons as a function of the circulatory needs of the patient, the controller including sensing and calculating apparatus for sensing and calculating the aortic pressure of the blood pump and the blood volume pumped with each stroke of the pistons.

6. A piston pump as recited in claim 5, wherein the sensing apparatus calculates the aortic pressure and blood stroke volume by sensing the piston positions, the air pressures in the piston chambers, the rates of change of such pressures, and the timing of such rates of change compared to the piston positions.

7. A piston pump as recited in claim 6 wherein the piston driven means normally drives only one of the pistons unless there is a failure in which case the other piston is driven and the first piston is not driven, and further comprising valve apparatus for automatically, pneumatically connecting the blood pump to the chamber of whichever piston is being driven and for pneumatically isolating the chamber of the inactive piston from the blood pump.

8. Apparatus for pneumatically driving a chambered blood pump comprising:

means for respectively delivering a measured amount of gas, at a selected pressure and during a selected first time period to at least one chamber of the blood pump, means for venting the chamber to the atmosphere for a selected second time period after each delivery of air, means for sensing the volume of gas delivered, the gas pressure during delivery, and the rate of change of such gas pressure during delivery, means for calculating from these sensed values the mean aortic pressure and blood volume pumped during the gas delivery step, means for comparing these calculated values with known reference values and calculating the differences between such values, and means for varying the gas volume, gas pressure, and the cycle rate of delivery of such gas volume to the blood pump as a function of such calculated differences.

9. A method of pneumatically driving a chambered blood pump including the steps of repetitively delivering a measured amount of gas, at a selected pressure and during a selected first time period to at least one chamber of the blood pump, venting the chamber to the atmosphere for a selected second time period after each gas delivery step, characterized by the steps of (a) sensing the volume of gas delivered, the gas pressure during delivery, and the rate of change of such gas pressure during delivery, (b) calculating from these sensed values the mean aortic pressure and blood volume pumped during the gas delivery step, (c) comparing these calculated values with known reference values and calculating the differences between such values and (d) varying the gas volume, gas pressure, and the cycle rate of delivery of such gas volume to the blood pump as a function of such calculated differences.

10. The blood pump driving method as recited in claim 9 wherein in step (c) the beat rate is not increased if the difference between the reference volume and the calculated volume exceeds a predetermined value.

* * * * *

UNITED STATES PATENT AND TRADEMARK OFFICE
CERTIFICATE OF CORRECTION

PATENT NO.  : 4,611,578

DATED       : September 16, 1986

INVENTOR(S) : Horst P. Helmes

It is certified that error appears in the above-identified patent and that said Letters Patent is hereby corrected as shown below:

Column 20, line 28, after "comprising" delete --ends,--.

Signed and Sealed this

Second Day of December, 1986

*Attest:*

DONALD J. QUIGG

*Attesting Officer*      *Commissioner of Patents and Trademarks*